United States Patent
Casillas et al.

(10) Patent No.: US 9,216,965 B2
(45) Date of Patent: Dec. 22, 2015

(54) AMINO-QUINOLINES AS KINASE INHIBITORS

(71) Applicant: GlaxoSmithKline Intellectual Property Development Limited, Brentford, Middlesex (GB)

(72) Inventors: Linda N. Casillas, Collegeville, PA (US); Michael P. Demartino, Collegeville, PA (US); Pamela A. Haile, Collegeville, PA (US); John F. Mehlmann, Collegeville, PA (US); Joshi M. Ramanjulu, Collegeville, PA (US); Robert Singhaus, Jr., Collegeville, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 14/396,559

(22) PCT Filed: Sep. 13, 2013

(86) PCT No.: PCT/US2013/059600
§ 371 (c)(1),
(2) Date: Oct. 23, 2014

(87) PCT Pub. No.: WO2014/043437
PCT Pub. Date: Mar. 20, 2014

(65) Prior Publication Data
US 2015/0094333 A1    Apr. 2, 2015

Related U.S. Application Data

(60) Provisional application No. 61/700,536, filed on Sep. 13, 2012, provisional application No. 61/767,378, filed on Feb. 21, 2013.

(51) Int. Cl.
*C07D 401/12*    (2006.01)

(52) U.S. Cl.
CPC .................................. *C07D 401/12* (2013.01)

(58) Field of Classification Search
None
See application file for complete search history.

(56) References Cited

U.S. PATENT DOCUMENTS

| | | | |
|---|---|---|---|
| 4,916,135 A | 4/1990 | Effland et al. | 514/254 |
| 5,457,105 A | 10/1995 | Barker | 514/234.5 |
| 5,710,158 A | 1/1998 | Myers et al. | 514/259 |
| 6,046,206 A | 4/2000 | Pamukcu et al. | 514/259 |
| 6,589,758 B1 | 7/2003 | Zhu | 435/15 |
| 6,809,097 B1 | 10/2004 | Thomas et al. | 514/235.2 |
| 7,282,504 B2 | 10/2007 | Armistead et al. | 514/275 |
| 7,452,887 B2 | 11/2008 | Dickson, Jr. et al. | 514/253.06 |
| 7,566,786 B2 | 7/2009 | Baldwin et al. | 546/159 |
| 7,569,577 B2 | 8/2009 | Hennequin et al. | 514/266.22 |
| 7,618,975 B2 | 11/2009 | Cai et al. | 514/262.1 |
| 7,709,479 B1 | 5/2010 | Mortlock et al. | 514/235.8 |
| 7,939,546 B2 | 5/2011 | Phiasivongsa et al. | 514/313 |
| 8,258,145 B2 | 9/2012 | Cai et al. | 514/266.21 |
| 2002/0026052 A1 | 2/2002 | Boschelli et al. | 546/122 |
| 2002/0147214 A1 | 10/2002 | Cockerill et al. | 514/311 |
| 2003/0105129 A1 | 6/2003 | Mortlock et al. | 514/313 |
| 2003/0212276 A1 | 11/2003 | Boschelli et al. | 546/153 |
| 2003/0216417 A1 | 11/2003 | Cumming | 514/266.4 |
| 2004/0242604 A1 | 12/2004 | Bhattacharya et al. | 514/266.4 |
| 2005/0070561 A1 | 3/2005 | Jung et al. | 514/266.23 |
| 2005/0137395 A1 | 6/2005 | Hong et al. | 540/575 |
| 2005/0267101 A1 | 12/2005 | Randle | 514/221 |
| 2006/0025327 A1 | 2/2006 | Sanchez et al. | 514/2 |
| 2006/0116357 A1 | 6/2006 | Heron et al. | 514/80 |
| 2006/0167035 A1 | 7/2006 | Schwede et al. | 514/291 |
| 2007/0021446 A1 | 1/2007 | Ehlert et al. | 514/266.2 |
| 2007/0299092 A1 | 12/2007 | Floyd, Jr. et al. | 514/266.1 |
| 2008/0032996 A1 | 2/2008 | Mitsuya et al. | 514/255.05 |
| 2008/0045568 A1 | 2/2008 | Deng et al. | 514/312 |
| 2008/0064878 A1 | 3/2008 | Aoki et al. | 546/277.4 |

(Continued)

FOREIGN PATENT DOCUMENTS

| | | |
|---|---|---|
| CN | 101362719 A | 2/2009 |
| GB | 2 345 486 A | 7/2000 |

(Continued)

OTHER PUBLICATIONS

Cavasotto, et al. Bioorg. & Med. Chem. Lett., 16: 1969-1974 (2006).
Kumar, et al. J. Clin. Oncol., 26: 1742-1751 (Apr. 1, 2008).
Manon, et al. J. Molec. Biol., 365: 160-174 (2007).
Robinett, et al. Bioorg. Med. Chem. Left., 17: 5886-5893 (2007).
Argast, et al. Molec. & Cell. Biochem., (Kluwer Academic Pubs) 268(1-2): 129-140 (2005).
PCT International Preliminary Report on Patentability & PCT Written Opinion of the International Searching Authority, PCT/US11/35521, Aug. 9, 2011.
PCT International Preliminary Report on Patentability & PCT Written Opinion of the International Searching Authority, PCT/US11/47183, Dec. 30, 2011.

(Continued)

*Primary Examiner* — Timothy R Rozof
(74) *Attorney, Agent, or Firm* — Kathryn A. Lutomski; William R. Majarian

(57) ABSTRACT

Disclosed are compounds having the formula:

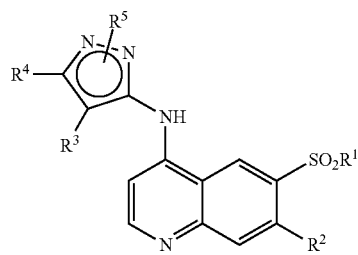

wherein $R^1$, $R^2 R^3$, $R^4$ and $R^5$ are as defined herein, and methods of making and using the same.

16 Claims, 4 Drawing Sheets

(56) References Cited

U.S. PATENT DOCUMENTS

| | | |
|---|---|---|
| 2008/0161305 A1 | 7/2008 | Forsyth et al. .............. 514/235.2 |
| 2008/0221132 A1 | 9/2008 | Cai et al. ................... 514/263.24 |
| 2008/0227811 A1 | 9/2008 | Chen ............................ 514/312 |
| 2008/0227812 A1 | 9/2008 | Chen ............................ 514/312 |
| 2008/0234267 A1 | 9/2008 | Lackey ...................... 514/235.2 |
| 2008/0269404 A1 | 10/2008 | Paul et al. ...................... 524/558 |
| 2008/0312273 A1 | 12/2008 | Hennequin ................... 514/311 |
| 2008/0318971 A1 | 12/2008 | Hewes ..................... 514/252.18 |
| 2009/0099106 A1 | 4/2009 | Phiasivongsa et al. ......... 514/43 |
| 2009/0270450 A1 | 10/2009 | Dakin et al. .................. 514/313 |
| 2010/0135999 A1 | 6/2010 | Nazare et al. .............. 424/133.1 |
| 2011/0053935 A1 | 3/2011 | Folkes et al. ............... 514/235.2 |
| 2011/0237629 A1 | 9/2011 | Meibom et al. .............. 514/340 |
| 2011/0256092 A1 | 10/2011 | Phiasivongsa et al. ...... 424/85.2 |
| 2012/0041024 A1 | 2/2012 | Charnley et al. ............. 514/313 |
| 2012/0053183 A1 | 3/2012 | Russu et al. ............. 514/252.17 |
| 2012/0070413 A1 | 3/2012 | Kim et al. .................... 424/85.4 |
| 2012/0122923 A1 | 5/2012 | Cosledan et al. ............. 514/313 |
| 2012/0165321 A1 | 6/2012 | Adams et al. ............... 514/223.2 |
| 2012/0219522 A1 | 8/2012 | Xi ............................... 424/85.4 |
| 2013/0018039 A1 | 1/2013 | Bodmer et al. .......... 514/210.21 |
| 2013/0023532 A1 | 1/2013 | Casillas et al. .............. 514/234.2 |
| 2013/0023534 A1 | 1/2013 | Casillas et al. .............. 514/236.5 |
| 2013/0053375 A1 | 2/2013 | Bury et al. .................. 514/228.2 |
| 2013/0345258 A1 | 12/2013 | Bury et al. ..................... 514/313 |
| 2014/0100234 A1 | 4/2014 | Knight et al. ............ 514/252.04 |
| 2014/0155396 A1 | 6/2014 | Bannen et al. .............. 514/234.5 |

FOREIGN PATENT DOCUMENTS

| | | |
|---|---|---|
| WO | WO 96/09294 A1 | 3/1996 |
| WO | WO 98/05647 A1 | 2/1998 |
| WO | WO 02/068394 A1 | 9/2002 |
| WO | WO 02/092571 A1 | 11/2002 |
| WO | WO 03/018022 A1 | 3/2003 |
| WO | WO 03/026666 A1 | 4/2003 |
| WO | EP 0 973 746 B1 | 9/2003 |
| WO | WO 2004/037814 A1 | 5/2004 |
| WO | WO 2007/045987 A1 | 4/2007 |
| WO | WO 2008/119771 A2 | 10/2008 |
| WO | WO 2011/112588 A1 | 9/2011 |
| WO | WO 2011/120025 A1 | 9/2011 |
| WO | WO 2011/120026 A1 | 9/2011 |
| WO | WO 2011/123609 A1 | 10/2011 |
| WO | WO 2011/140442 A1 | 11/2011 |
| WO | WO 2012/021580 A1 | 2/2012 |
| WO | WO 2012/122011 A2 | 9/2012 |
| WO | WO 2013/025958 A1 | 2/2013 |
| WO | WO 2014/043437 A1 | 3/2014 |
| WO | WO 2014/043446 A1 | 3/2014 |
| WO | WO 2014/128622 A1 | 8/2014 |

OTHER PUBLICATIONS

PCT International Preliminary Report on Patentability & PCT Written Opinion of the International Searching Authority, PCT/US12/27439, Jun. 7, 2012.
PCT International Preliminary Report on Patentability & PCT Written Opinion of the International Searching Authority, PCT/US12/51247, Oct. 23, 2012.
PCT International Preliminary Report on Patentability & PCT Written Opinion of the International Searching Authority, PCT/US13/59600, Jan. 29, 2014.
PCT International Preliminary Report on Patentability & PCT Written Opinion of the International Searching Authority, PCT/US13/59619, Jan. 29, 2014.
EP Supplementary Search Report for PCT/US11/030103, dated Sep. 23, 2013.
EP Supplementary Search Report for PCT/US11/030104, dated Sep. 17, 2013.
EP Supplementary Search Report for PCT/US11/35521, dated Oct. 23, 2013.
EP Supplementary Search Report for PCT/US11/47183, dated Dec. 17, 2013.
Sheth, et al. Archives of Biochemistry & Biophysics, 503: 191-201 (2010).
Cai, et al. Journal of Medicinal Chemistry, 53(5): 2000-2009 (2010).
EP Supplementary Search Report for PCT/US2012/027439, dated Dec. 16, 2014.
Amendment, U.S. Appl. No. 14/283,352, filed Apr. 7, 2015.
Amendment, U.S. Appl. No. 14/397,218, filed May 21, 2015.
Amendment, U.S. Appl. No. 14/002,147, filed May 15, 2015.
Amendment, U.S. Appl. No. 13/696,603, filed on Feb. 6, 2015.
Foley et al., Pediatric Rheumatology, 2013,11 (Suppl):A3 (published Nov. 8, 2013; presented 7th Congress of ISSAID, Lusanne, Switzerland May 22-26, 2013).
Poster: C.R. Hanning, AAI Annual Meeting, Pittsburgh PA (May 4, 2014).
Poster: B. J. Votta, et al., Keystone Symposia on Innate Immunity, Keystone, CO (Mar. 7, 2012).
EP Supplementary Search Report for PCT/US2012/051247, dated Feb. 18, 2015.
Amendment, U.S. Appl. No. 14/239,193, filed on May 12, 2015.
Tigno-Aranjuez, Genes & Development, vol. 24, 2666-2677, 2010.
Arostegui, et al., *Arthritis & Rheumatism*, 56(11):3805-3813 (2007).
Biancheri, et al., *Digestive and Liver Disease, Abstract*, 45S:S71 (2013).
Body-Malapel, et al., *Laboratory Investigation*, 88:318-327 (2008).
Carreno, et al., *Acta Ophthalmologica, Abstract*, 2014.
Corridoni, et al., *PNAS*, 110(42):16999-17004 (2013).
Denou, et al., *EMBO Molecular Medicine*, 7(3):259-274 (2015).
Dharancy, et al., *Gastroenterology*, 138:1546-1556 (2010).
Du, et al., *Kidney International*, 84:265-276 (2013).
Ermann, et al., *PNAS*, E2559-E2566 (2014).
Ferrero-Miliani, et al., *Clinical and Experimental Immunology*, 147:227-235 (2006).
Foley, et al., *Pediatric Rheumatology*, 11 (Suppl. 1):A3 (2013).
Geddes, et al., *Infection and Immunity*, 78(12):5107-5115 (2010).
Goh, et al., *The Journal of Immunology*, 191:2691-2699 (2013).
Goncalves, et al., *The Scandanavian Journal of Immunology*, 73:428-435 (2011).
Hedegaard, et al., *Plos One*, 6(5):e20253 (2011).
Heinhuis, et al., *Ann Rheum Dis*, 69:1866-1872 (2009).
Hysi, et al., *Human Molecular Genetics*, 14(7):935-941 (2005).
Ikeda, et al., *Arthritis Research & Therapy*, 16:R89 (2014).
Jamontt, et al., *Journal of Immunology*, 190:2948-2958 (2013).
Jun, et al., *Journal of Leukocyte Biology*, 94:927-932 (2013).
Kruger, et al., *European Society for Organ Transplantation*, 20:600-607 (2007).
Kvarnhammar, et al., *Plos One*, 8(7):e68701 (2013).
Liu, et al., *Journal of Biological Sciences*, 11(5):525-535 (2015).
McGovern, et al., *Human Molecular Genetics*, 14(10):1245-1250 (2005).
Murias, et al., *Pediatric Rheumatology*, 12(Suppl. 1):P293 (2014).
Nachbur, et al., *Nature Communications*, 6:6442 (2015).
Natarajan, et al., *Journal of Neuroimmunology*, 265:51-60 (2013).
Oh, et al., *Plos Pathogens*, 9(5):e1003351 (2013).
Ospelt, et al., *Arthritis & Rheumatism*, 60(2):355-363 (2009).
Paim-Marque, et al., *Pediatric Rheumatology*, 12(Suppl. 1):P272 (2014).
Penack, et al., *The Journal of Experimental Medicine*, 206(10):2101-2110 (2009).
Peng, et al., *International Immunopharmacology*, 13:440-445 (2012).
Pillai, et al., *Seminars in Ophthalmology*, 28(5-6):327-332 (2013).
Plantinga, et al., *Rheumatology*, 52:806-814 (2013).
Rebane, et al., *The Journal of Allergy & Clinical Immunology*, 129:1297-1306 (2012).
Rosenzweig, et al., *Arthritis & Rheumatism*, 62(4):1051-1059 (2010).
Rosenzweig, et al., *Inflammation Research*, 60:705-714 2011).
Rosenzweig, et al., *Investigative Ophthalmology & Visual Science*, 50(4):1746-1753 (2009).
Rosenzweig, et al., *Investigative Ophthalmology & Visual Science*, 50(4):1739-1745 (2009).
Saha, et al., *Cell Host & Microbe*, 5:137-150 (2009).
Sfriso, et al., *Autoimmunity Reviews*, 12:44-51 (2012).

(56) References Cited

OTHER PUBLICATIONS

Shaw, et al., *Immunity*, 34:75-84 (2011).
Shigeoka, et al., *The Journal of Immunology*, 184:2297-2304 (2010).
Uehara, et al., *Diagnostic Pathology*, 4(23):1746 (2009).
Vieira, et al., *The Journal of Immunology*, 188:5116-5122 (2012).
Walsh, et al., *Cytokine & Growth Factor Reviews*, 24:91-104 (2013).
Wiken, et al., *The Journal of Clinical Immunology*, 29:78-89 (2009).
Yu, et al., *Plos One*, 6(8):e23855 (2011).
Zhou, et al., *Diabetes & Metabolism*, 38:538-543 (2012).

AMINO-QUINOLINES AS KINASE INHIBITORS

This application is a 371 of International Application No. PCT/US2013/059600, filed 13 Sep. 2013, which claims the benefit of U.S. Provisional Application Nos. 61/767,378, filed 21 Feb. 2013 and 61/700,536, filed 13 Sep. 2012, which are incorporated herein in their entireties.

BACKGROUND OF THE INVENTION

1. Field of the Invention

The present invention relates to 4-amino-quinolines that inhibit RIP2 kinase and methods of making and using the same. Specifically, the present invention relates to substituted 4-amino-quinolines as RIP2 kinase inhibitors.

2. Background of the Invention

Receptor interacting protein-2 (RIP2) kinase, which is also referred to as CARD3, RICK, CARDIAK, or RIPK2, is a TKL family serine/threonine protein kinase involved in innate immune signaling. RIP2 kinase is composed of an N-terminal kinase domain and a C-terminal caspase-recruitment domain (CARD) linked via an intermediate (IM) region ((1998) *J. Biol. Chem.* 273, 12296-12300; (1998) *Current Biology* 8, 885-889; and (1998) *J. Biol. Chem.* 273, 16968-16975). The CARD domain of RIP2 kinase mediates interaction with other CARD-containing proteins, such as NOD1 and NOD2 ((2000) *J. Biol. Chem.* 275, 27823-27831 and (2001) *EMBO reports* 2, 736-742). NOD1 and NOD2 are cytoplasmic receptors which play a key role in innate immune surveillance. They recognize both gram positive and gram negative bacterial pathogens and are activated by specific peptidoglycan motifs, diaminopimelic acid (i.e., DAP) and muramyl dipeptide (MDP), respectively ((2007) *J Immunol* 178, 2380-2386).

Following activation, RIP2 kinase associates with NOD1 or NOD2 and appears to function principally as a molecular scaffold to bring together other kinases (TAK1, IKKα/β/γ) involved in NF-κB and mitogen-activated protein kinase activation ((2006) *Nature Reviews Immunology* 6, 9-20). RIP2 kinase undergoes a K63-linked polyubiquitination on lysine-209 which facilitates TAK1 recruitment ((2008) *EMBO Journal* 27, 373-383). This post-translational modification is required for signaling as mutation of this residue prevents NOD1/2 mediated NF-kB activation. RIP2 kinase also undergoes autophosphorylation on serine-176, and possibly other residues ((2006) *Cellular Signalling* 18, 2223-2229). Studies using kinase dead mutants (K47A) and non-selective small molecule inhibitors have demonstrated that RIP2 kinase activity is important for regulating the stability of RIP2 kinase expression and signaling ((2007) *Biochem J* 404, 179-190 and (2009) *J. Biol. Chem.* 284, 19183-19188).

Dysregulation of RIP2-dependent signaling has been linked to autoinflammatory diseases. Gain-of-function mutations in the NACHT-domain of NOD2 cause Blau Syndrome, early-onset sarcoidosis, a pediatric granulomateous disease characterized by uveitis, dermatitis, and arthritis ((2001) *Nature Genetics* 29, 19-20; (2005) *Journal of Rheumatology* 32, 373-375; (2005) *Current Rheumatology Reports* 7, 427-433; (2005) *Blood* 105, 1195-1197; (2005) *European Journal of Human Genetics* 13, 742-747; (2006) *American Journal of Ophthalmology* 142, 1089-1092; (2006) *Arthritis & Rheumatism* 54, 3337-3344; (2009) *Arthritis & Rheumatism* 60, 1797-1803; and (2010) *Rheumatology* 49, 194-196). Mutations in the LRR-domain of NOD2 have been strongly linked to susceptibility to Crohn's Disease ((2002) *Am. J. Hum. Genet.* 70, 845-857; (2004) *European Journal of Human Genetics* 12, 206-212; (2008) *Mucosal Immunology* (2008) 1 (Suppl 1), S5-S9. 1, S5-S9; (2008) *Inflammatory Bowel Diseases* 14, 295-302; (2008) *Experimental Dermatology* 17, 1057-1058; (2008) *British Medical Bulletin* 87, 17-30; (2009) *Inflammatory Bowel Diseases* 15, 1145-1154 and (2009) *Microbes and Infection* 11, 912-918). Mutations in NOD1 have been associated with asthma ((2005) *Hum. Mol. Genet.* 14, 935-941) and early-onset and extraintestinal inflammatory bowel disease ((2005) *Hum. Mol. Genet.* 14, 1245-1250). Genetic and functional studies have also suggested a role for RIP2-dependent signaling in a variety of other granulomateous disorders, such as sarcoidosis ((2009) *Journal of Clinical Immunology* 29, 78-89 and (2006) *Sarcoidosis Vasculitis and Diffuse Lung Diseases* 23, 23-29) and Wegner's Granulomatosis ((2009) *Diagnostic Pathology* 4, 23).

A potent, selective, small molecule inhibitor of RIP2 kinase activity would block RIP2-dependent pro-inflammatory signaling and thereby provide a therapeutic benefit in autoinflammatory diseases characterized by increased and/or dysregulated RIP2 kinase activity.

SUMMARY OF THE INVENTION

The invention is directed to 6,7-disubstituted-4-amino-quinolines. Specifically, the invention is directed to a compound according to Formula (I):

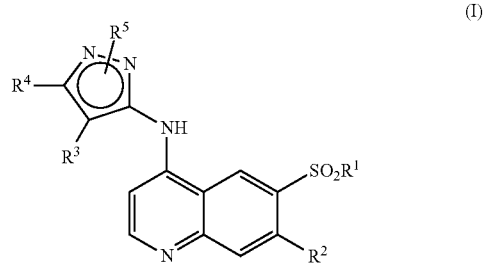

(I)

wherein:

$R^1$ is $(C_1-C_6)$alkyl, halo$(C_1-C_6)$alkyl, $(C_3-C_6)$cycloalkyl, or 4-6 membered heterocycloalkyl, wherein:

said $(C_1-C_6)$alkyl is optionally substituted by one group selected from the group consisting of cyano, hydroxyl, $(C_1-C_6)$alkoxy, $(C_1-C_6)$alkoxy$(C_2-C_6)$alkoxy, —$CO_2H$, —$CO_2(C_1-C_4)$alkyl, —$SO_2(C_1-C_4)$alkyl, $(C_3-C_6)$cycloalkyl, and 4-6 membered heterocycloalkyl, wherein said $(C_3-C_6)$cycloalkyl or 4-6 membered heterocycloalkyl is optionally substituted by 1 or 2 groups each independently selected from the group consisting of halogen, —$CF_3$, hydroxyl, amino, $((C_1-C_4)$alkyl)amino-, $((C_1-C_4)$alkyl)$((C_1-C_4)$alkyl)amino-, $(C_1-C_4)$alkyl, hydroxy$(C_1-C_4)$alkyl and $(C_1-C_4)$alkoxy, said $(C_3-C_6)$cycloalkyl or 4-6 membered heterocycloalkyl is optionally substituted by 1-3 groups each independently selected from the group consisting of halogen, —$CF_3$, hydroxyl, cyano, amino, $((C_1-C_4)$alkyl)amino-, $((C_1-C_4)$alkyl)$((C_1-C_4)$alkyl)amino-, $(C_1-C_4)$alkyl, hydroxy$(C_1-C_4)$alkyl-, oxo and $(C_1-C_4)$alkoxy, and $R^2$ is fluoro, hydroxy, $(C_1-C_6)$alkoxy-, halo$(C_1-C_6)$alkoxy-, $(C_1-C_4)$alkoxy$(C_2-C_6)$alkoxy-, halo$(C_1-C_4)$alkoxy$(C_2-C_6)$alkoxy-, hydroxy$(C_2-C_6)$alkoxy-, $(C_3-C_6)$cycloalkyl$(C_1-C_4)$alkoxy-, $(C_3-C_6)$cycloalkyl-oxy-, 4-6 membered-heterocycloalkyl$(C_1-C_4)$alkoxy-, or 4-6 membered-heterocycloalkyl-oxy-, wherein the halo$(C_1-C_6)$alkyl moiety of the halo$(C_1-C_6)$alkoxy- and the halo$(C_1-C_4)$alkyl moiety of the halo$(C_1-C_4)$alkoxy$(C_2-C_6)$alkoxy- groups contain 1, 2 or 3 fluoro atoms, wherein the (C₃-C₆)cycloalkyl moiety of the (C₃-C₆)cycloalkyl(C₁-C₄)alkoxy- or (C₃-C₆)cycloalkoxy- is optionally substituted by a group selected from the group consisting of cyano, halo, hydroxyl, (C₁-C₆)alkoxy and (C₁-C₄)alkoxy(C₂-C₆)alkoxy, and wherein the 4-6 membered heterocycloalkyl moiety of the 4-6 membered heterocycloalkyl(C₁-C₄)alkoxy-, or 4-6 membered-heterocycloalkyl-oxy- is optionally substituted by a group selected from the group consisting of cyano, halo, hydroxyl, (C₁-C₆)alkoxy and (C₁-C₄)alkoxy(C₂-C₆)alkoxy;

R³ is H or methyl;
R⁴ is H, methyl, or trifluoromethyl; and
R⁵ is H or (C₁-C₃)alkyl;

or a salt, particularly a pharmaceutically acceptable salt, thereof; provided the compound is not:

6-(tert-butylsulfonyl)-N-(4,5-dimethyl-1H-pyrazol-3-yl)-7-methoxyquinolin-4-amine,
2-((4-((4,5-dimethyl-1H-pyrazol-3-yl)amino)-7-methoxyquinolin-6-yl)sulfonyl)-2-methylpropan-1-ol,
N-(4,5-dimethyl-1H-pyrazol-3-yl)-7-methoxy-6-((tetrahydro-2H-pyran-4-yl)sulfonyl)quinolin-4-amine,
N-(4,5-dimethyl-1H-pyrazol-3-yl)-6-((2,2-dimethyltetrahydro-2H-pyran-4-yl)sulfonyl)-7-methoxyquinolin-4-amine,
N-(4,5-dimethyl-1H-pyrazol-3-yl)-7-methoxy-6-((4-methyltetrahydro-2H-pyran-4-yl)sulfonyl)quinolin-4-amine,
N-(4,5-dimethyl-1H-pyrazol-3-yl)-7-methoxy-6-((2-methoxyethyl)sulfonyl)quinolin-4-amine,
N-(4,5-dimethyl-1H-pyrazol-3-yl)-7-methoxy-6-(((3R,4R)-3-methyltetrahydro-2H-pyran-4-yl)sulfonyl)quinolin-4-amine,
N-(4,5-dimethyl-1H-pyrazol-3-yl)-6-(((2R,6S)-2,6-dimethyltetrahydro-2H-pyran-4-yl)sulfonyl)-7-methoxyquinolin-4-amine,
6-(tert-butylsulfonyl)-4-((4,5-dimethyl-1H-pyrazol-3-yl)amino)quinolin-7-ol,
2-{[4-[(4,5-dimethyl-1H-pyrazol-3-yl)amino]-7-(methyloxy)-6-quinolinyl]sulfonyl}ethanol,
N-(4,5-dimethyl-1H-pyrazol-3-yl)-6-[(1-methylethyl) sulfonyl]-7-(methyloxy)-4-quinolinamine,
6-(isopropyl-sulfonyl)-7-methoxy-N-(4-methyl-5-(trifluoromethyl)-1H-pyrazol-3-yl)quinolin-4-amine,
6-(tert-butylsulfonyl)-7-methoxy-N-(4-methyl-5-(trifluoromethyl)-1H-pyrazol-3-yl)quinolin-4-amine,
6-(tert-butylsulfonyl)-N-(4,5-dimethyl-1H-pyrazol-3-yl)-7-ethoxyquinolin-4-amine,
7-methoxy-N-(4-methyl-5-(trifluoromethyl)-1H-pyrazol-3-yl)-6-((tetrahydro-2H-pyran-4-yl)sulfonyl) quinolin-4-amine,
2-((6-(tert-butylsulfonyl)-4-((4,5-dimethyl-1H-pyrazol-3-yl)amino)quinolin-7-yl)oxy)ethanol,
6-(tert-butylsulfonyl)-7-(difluoromethoxy)-N-(4,5-dimethyl-1H-pyrazol-3-yl)quinolin-4-amine, or
7-(difluoromethoxy)-N-(4,5-dimethyl-1H-pyrazol-3-yl)-6-((tetrahydro-2H-pyran-4-yl)sulfonyl)quinolin-4-amine, or a salt thereof.

The compounds according to Formula (I), or salts, particularly pharmaceutically acceptable salts, thereof, are inhibitors of RIP2 kinase.

Accordingly, the present invention is also directed to a method of inhibiting RIP2 kinase which method comprises contacting a cell with a compound according to Formula (I), or a salt, particularly a pharmaceutically acceptable salt, thereof.

The invention is further directed to a method of treating a RIP2 kinase-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Examples of RIP2 kinase-mediated diseases or disorders include uveitis, Crohn's disease, ulcerative colitis, early-onset and extraintestinal inflammatory bowel disease and granulomatous disorders, such as sarcoidosis, Blau syndrome, early-onset sarcoidosis and Wegner's Granulomatosis.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a RIP2 kinase-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE INVENTION

Figure 1:
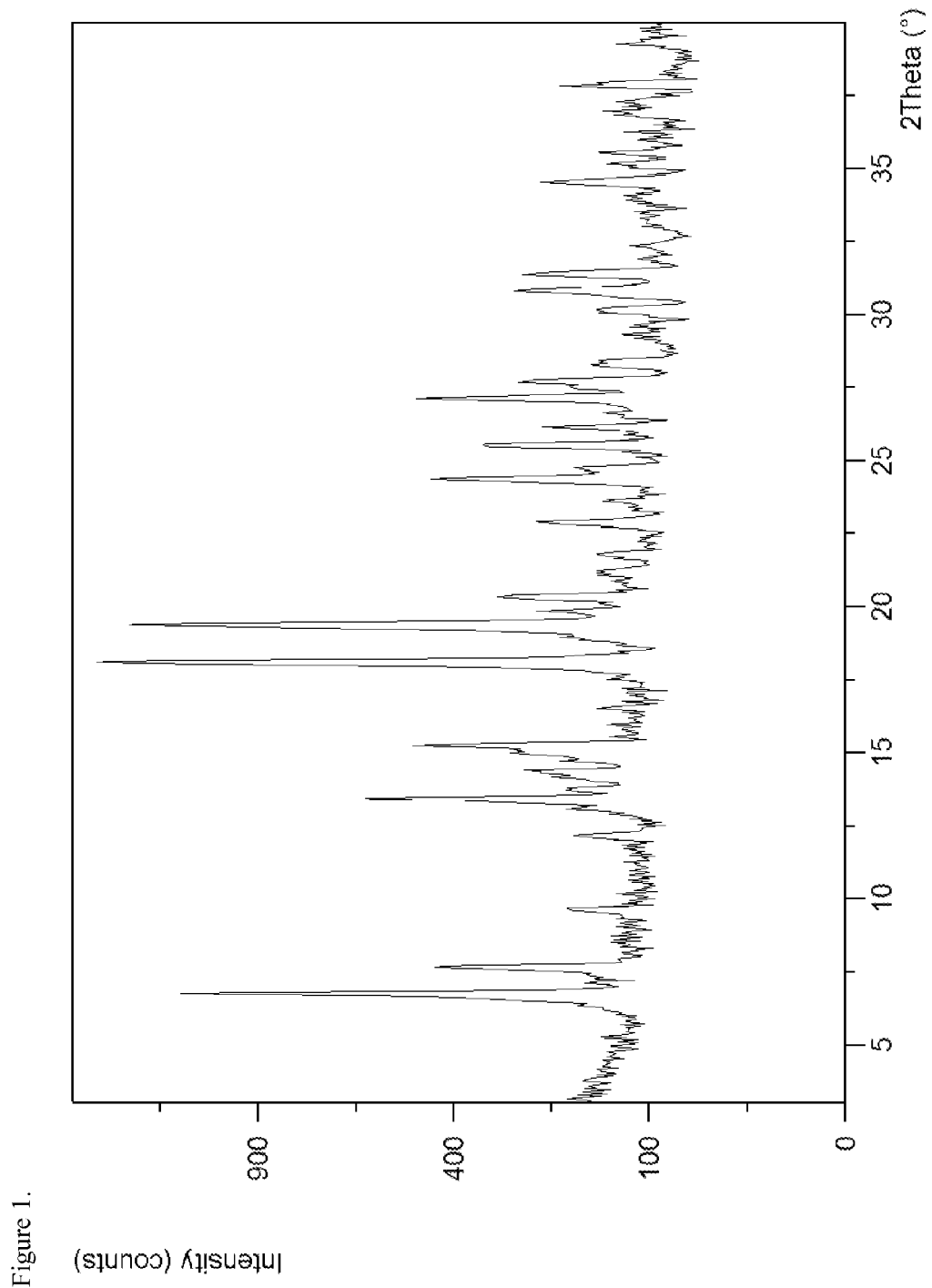
FIG. 1 is a powder x-ray powder diffraction (PXRD) pattern of a crystalline form of (R)-1-((6-(tert-butylsulfonyl)-4-((3,4-dimethyl-1H-pyrazol-5-yl)amino)quinolin-7-yl)oxy)propan-2-ol, hydrochloride.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

It will also be appreciated by those skilled in the art that the pyrazolyl moiety in Formula (I) may exist as pyrazole isomers represented by Formula (I-A) and Formula (I-B):

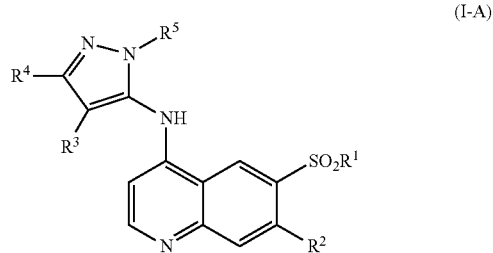

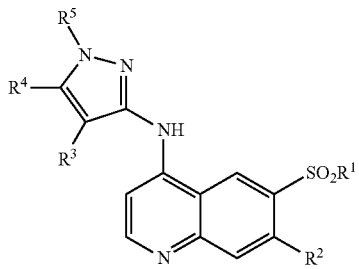

(I-B)

When R⁵ is (C₁-C₃)alkyl, the compounds of this invention may exist as either one of the regioisomers represented by Formula (I-A) or Formula (I-B), or as a mixture thereof. When R⁵ is H, the compounds of this invention may be named as one of the regioisomers represented by Formula (I-A) or Formula (I-B). For example when R³ and R⁴ are both methyl and R⁵ is H, it will be understood that the resulting pyrazolyl moiety may be named as either a 3,4-dimethyl-1H-pyrazol-5-yl moiety or a 4,5-dimethyl-1H-pyrazol-3-yl moiety.

As used herein, the term "alkyl" represents a saturated, straight or branched hydrocarbon moiety. Exemplary alkyls include, but are not limited to methyl (Me), ethyl (Et), n-propyl, isopropyl, n-butyl, s-butyl, isobutyl, t-butyl and pentyl. The term "C₁-C₄ alkyl" refers to an alkyl group or moiety containing from 1 to 4 carbon atoms.

When the term "alkyl" is used in combination with other substituent groups, such as "haloalkyl" or "hydroxyalkyl" or "arylalkyl", the term "alkyl" is intended to encompass a divalent straight or branched-chain hydrocarbon radical. For example, "arylalkyl" is intended to mean the radical alkylaryl, wherein the alkyl moiety thereof is a divalent straight or branched-chain carbon radical and the aryl moiety thereof is as defined herein, and is represented by the bonding arrangement present in a benzyl group (—CH₂-phenyl); "halo(C₁-C₄)alkyl" or "(C₁-C₄)haloalkyl" is intended to mean a radical having one or more halogen atoms, which may be the same or different, at one or more carbon atoms of an alkyl moiety containing from 1 to 4 carbon atoms, which is straight or branched-chain carbon radical, and is represented by a trifluoromethyl group (—CF₃).

As used herein, the term "cycloalkyl" refers to a non-aromatic, saturated, cyclic hydrocarbon ring. The term "(C₃-C₇)cycloalkyl" refers to a non-aromatic cyclic hydrocarbon ring having from three to eight ring carbon atoms. Exemplary "(C₃-C₈)cycloalkyl" groups include cyclopropyl, cyclobutyl, cyclopentyl, cyclohexyl, and cycloheptyl.

"Alkoxy" refers to a group containing an alkyl radical attached through an oxygen linking atom. The term "(C₁-C₄) alkoxy" refers to a straight- or branched-chain hydrocarbon radical having at least 1 and up to 4 carbon atoms attached through an oxygen linking atom. Exemplary "(C₁-C₄) alkoxy" groups include, but are not limited to, methoxy, ethoxy, n-propoxy, isopropoxy, n-butoxy, s-butoxy, isobutoxy, and t-butoxy.

"Aryl" represents a group or moiety comprising an aromatic, monocyclic or bicyclic hydrocarbon radical containing from 6 to 10 carbon ring atoms, which may be fused to one or more cycloalkyl rings. Generally, in the compounds of this invention, aryl is phenyl.

A heterocyclic group or moiety is a cyclic group or moiety having as ring members atoms of at least two different elements (carbon and one or more of nitrogen, oxygen and/or sulfur), which cyclic group or moiety may be saturated or partially unsaturated (non-aromatic; e.g., a heterocycloalkyl group or moiety) or fully unsaturated (aromatic; e.g., a heteroaryl group or moiety).

"Heterocycloalkyl" represents a group or moiety comprising a non-aromatic, monocyclic or bicyclic radical, which is saturated or partially unsaturated, containing 3 to 10 ring atoms, unless otherwise specified, which includes 1 to 4 heteroatoms selected from nitrogen, oxygen and sulfur. Illustrative examples of heterocycloalkyls include, but are not limited to, azetidinyl, oxetanyl, pyrrolidyl (or pyrrolidinyl), piperidinyl, piperazinyl, morpholinyl, tetrahydro-2H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1] octyl, azabicylo[3.3.1]nonyl, azabicylo[4.3.0]nonyl, oxabicylo[2.2.1]heptyl and 1,5,9-triazacyclododecyl.

Heterocycloalkyl groups include 4-membered heterocycloalkyl groups containing one heteroatom, such as oxetanyl, thietanyl and azetidinyl.

Heterocycloalkyl groups include 5-membered heterocycloalkyl groups containing one heteroatom selected from nitrogen, oxygen and sulfur and optionally containing one or two additional nitrogen atoms, or optionally containing one additional oxygen or sulfur atom, such as pyrrolidyl (or pyrrolidinyl), tetrahydrofuryl (or tetrahydrofuranyl), tetrahydrothienyl, dihydrofuryl, oxazolinyl, thiazolinyl, imidazolinyl, pyrazolinyl, 1,3-dioxolanyl, and 1,3-oxathiolan-2-on-yl.

Heterocycloalkyl groups are 6-membered heterocycloalkyl groups containing one heteroatom selected from nitrogen, oxygen and sulfur and optionally containing one or two additional nitrogen atoms or one additional oxygen or sulfur atom, such as piperidyl (or piperidinyl), piperazinyl, morpholinyl, thiomorpholinyl, 1,1 dioxoido-thiomorpholin-4-yl, tetrahydropyranyl, dihydropyranyl, tetrahydro-2H-1,4-thiazinyl, 1,4-dioxanyl, 1,3-oxathianyl, and 1,3-dithianyl.

"Heteroaryl" refers to a group or moiety comprising an aromatic monocyclic or bicyclic radical, containing 5 to 10 ring atoms, including 1 to 4 heteroatoms selected from nitrogen, oxygen and sulfur. This term also encompasses bicyclic heterocyclic-aryl compounds containing an aryl ring moiety fused to a heterocycloalkyl ring moiety, containing 5 to 10 ring atoms, including 1 to 4 heteroatoms selected from nitrogen, oxygen and sulfur. Illustrative examples of heteroaryls include, but are not limited to, thienyl, pyrrolyl, imidazolyl, pyrazolyl, furyl (or furanyl), isothiazolyl, isoxazolyl, oxazolyl, oxadiazolyl, thiazolyl, pyridyl (or pyridinyl), pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl, and isothiazolyl.

In some embodiments, the heteroaryl groups are 5-membered and/or 6-membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl (furanyl), isothiazolyl, isoxazolyl, oxazolyl, oxadiazolyl, thiazolyl, triazolyl and tetrazolyl or pyridyl, pyrazinyl, pyrimidinyl, pyridazinyl and triazinyl.

In other embodiments, the heteroaryl groups are 9-membered or 10-membered monocyclic heteroaryl groups.

Selected 9-10 membered heteroaryl groups contain one nitrogen, oxygen or sulfur ring heteroatom, and optionally contain 1, 2, 3 or 4 additional nitrogen ring atoms.

Heteroaryl groups include a 9-membered heteroaryl group, which includes benzothienyl, benzofuranyl, indolyl, indolinyl, isoindolyl, isoindolinyl, indazolyl, indolizinyl, isobenzofuryl, 2,3-dihydrobenzofuryl, benzoxazolyl, benzothiazolyl, benzimidazolyl, benzoxadiazolyl, benzothiadiazolyl, benzotriazolyl, 1,3-benzoxathiol-2-on-yl(2-oxo-1,3-benzoxathiolyl), purinyl and imidazopyridinyl.

Heteroaryl groups include a 10-membered heteroaryl group, which includes chromenyl, chromanyl, quinolyl, isoquinolyl, phthalazinyl, naphthridinyl, quinazolinyl, quinoxalinyl, 4H-quinolizinyl, tetrahydroquinolinyl, cinnolinyl, and pteridinyl.

It is to be understood that the terms heterocyclic, heteroaryl, and heterocycloalkyl are intended to encompass stable heterocyclic groups where a ring nitrogen heteroatom is optionally oxidized (e.g., heterocyclic groups containing an N-oxide, such as pyridine-N-oxide) or where a ring sulfur heteroatom is optionally oxidized (e.g., heterocyclic groups containing sulfones or sulfoxide moieties, such as tetrahydrothienyl-1-oxide (a tetrahydrothienyl sulfoxide) or tetrahydrothienyl-1,1-dioxide (a tetrahydrothienyl sulfone)).

"Oxo" represents a double-bonded oxygen moiety; for example, if attached directly to a carbon atom forms a carbonyl moiety (C=O). The terms "halogen" and "halo" represent chloro, fluoro, bromo or iodo substituents. "Hydroxy" or "hydroxyl" is intended to mean the radical —OH.

As used herein, the terms "compound(s) of the invention" or "compound(s) of this invention" mean a compound of Formula (I) as defined herein, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di-, tri-, and hemi-hydrates)), and mixtures of various forms (a hydrate of a salt).

As used herein, the term "optionally substituted" indicates that a group (such as an alkyl, cycloalkyl, alkoxy, heterocycloalkyl, aryl, or heteroaryl group) or ring or moiety (such as a carbocyclic or heterocyclic ring or moiety) may be unsubstituted, or the group, ring or moiety may be substituted with one or more substituent(s) as defined. In the case where groups may be selected from a number of alternative groups, the selected groups may be the same or different.

The term "independently" means that where more than one substituent is selected from a number of possible substituents, those substituents may be the same or different.

In a still further embodiment, $R^1$ is an optionally substituted $(C_1-C_6)$alkyl, $(C_3-C_6)$cycloalkyl, or 4-6-membered heterocycloalkyl group, wherein
said $(C_1-C_6)$alkyl is optionally substituted by hydroxyl, $(C_1-C_2)$alkoxy, $(C_1-C_2)$alkoxy$(C_2-C_3)$alkoxy-, $(C_3-C_6)$cycloalkyl (optionally substituted by $(C_1-C_4)$alkyl or hydroxy$(C_1-C_4)$alkyl) or 4-6-membered heterocycloalkyl (optionally substituted by $(C_1-C_4)$alkyl or halogen), and
said $(C_3-C_6)$cycloalkyl or 4-6-membered heterocycloalkyl is optionally substituted by 1 or 2 groups each independently selected from the group consisting of halogen, $(C_1-C_4)$alkyl, and hydroxy$(C_1-C_4)$alkyl-,
wherein any of said 4-6 membered heterocycloalkyl groups contains 1 heteroatom selected from N, O and S. Particularly, in this embodiment, when $R^1$ is an optionally substituted $(C_1-C_6)$alkyl, said $(C_1-C_6)$alkyl is optionally substituted by a group selected from the group consisting of hydroxyl, $(C_1-C_2)$alkoxy, and $(C_1-C_2)$alkoxy$(C_2-C_3)$alkoxy-.

When $R^1$ is a heterocycloalkyl group, it is to be understood that the heterocycloalkyl group is bonded to the sulfur atom of the —$SO_2R^1$ moiety by a ring carbon atom.

In another embodiment, $R^1$ is halo$(C_1-C_4)$alkyl containing 1-9 halogen atoms. In specific embodiments, $R^1$ is halo$(C_1-C_3)$alkyl, specifically a halo$(C_1-C_2)$alkyl containing 1, 2, 3, 4, or 5 halogen atoms, specifically fluorine atoms (fluoro).

In one embodiment of this invention, $R^1$ is an unsubstituted $(C_1-C_5)$alkyl. In a further embodiment of the compounds of this invention, $R^1$ is an unsubstituted $(C_1-C_4)$alkyl group. In another embodiment, $R^1$ is a $(C_1-C_5)$alkyl group, specifically a $(C_1-C_4)$alkyl group, substituted by a hydroxyl, $(C_1-C_2)$alkoxy, or $(C_1-C_2)$alkoxy$(C_2-C_3)$alkoxy- group. In a further embodiment, $R^1$ is a $(C_1-C_5)$alkyl, specifically a $(C_1-C_4)$alkyl, substituted by one hydroxyl group. In yet another embodiment, $R^1$ is a 4-6-membered heterocycloalkyl group optionally substituted by 1 or 2 independently selected $(C_1-C_4)$alkyl or fluoro groups. In still another embodiment, $R^1$ is a tetrahydropyranyl group.

In one embodiment, $R^1$ is —$CH_3$, —$CH(CH_3)_2$, or —$C(CH_3)_3$. In another embodiment, $R^1$ is —$CH_2CH_2OH$ or —$C(CH_3)_2CH_2CH_2OH$. In another embodiment, $R^1$ is —$CF_3$, —$CHF_2$, —$CFH_2$, or —$CF(CH_3)_2$. In yet another embodiment, $R^1$ is tetrahydro-2H-pyran-4-yl. In further embodiment, $R^1$ is —$CH_2CH_2OCH_3$, —$CH_2CH_2CH_2OH$, —$CH_2CH(CH_3)_2$, or —$CH_2CH(CH_3)OH$. In a still further embodiment, $R^1$ is oxiran-3-yl, 3-methyl-oxirany-3-yl, 4-methyl-tetrahydro-2H-pyran-4-yl, 3-methyltetrahydrofuran-3-yl or 2-methyltetrahydrofuran-3-yl. In specific embodiments, $R^1$ is —$C(CH_3)_3$.

In yet another embodiment of the compounds of this invention, $R^2$ is halogen, hydroxy, $(C_1-C_5)$alkoxy-, halo$(C_1-C_4)$alkoxy-, $(C_1-C_4)$alkoxy$(C_2-C_6)$alkoxy-, halo$(C_1-C_4)$alkoxy$(C_2-C_6)$alkoxy-, hydroxy$(C_2-C_6)$alkoxy-, $(C_3-C_6)$cycloalkyl$(C_1-C_4)$alkoxy-, $(C_3-C_6)$cycloalkyl-oxy-, 4-6 membered-heterocycloalkyl$(C_1-C_4)$alkoxy-, or 4-6 membered-heterocycloalkyl-oxy-.

In another embodiment of this invention, $R^2$ is fluoro, hydroxy, $(C_1-C_4)$alkoxy-, halo$(C_1-C_3)$alkoxy-, $(C_3-C_6)$cycloalkyl$(C_1-C_3)$alkoxy-, 5-6-membered-heterocycloalkyl-oxy-, $(C_1-C_3)$alkoxy$(C_2-C_4)$alkoxy-, halo$(C_1-C_2)$alkoxy$(C_2-C_4)$alkoxy-, or hydroxy$(C_2-C_4)$alkoxy-.

In a still further embodiment, $R^2$ is fluoro or $R^2$ is halo$(C_1-C_6)$alkoxy-, $(C_1-C_4)$alkoxy$(C_2-C_6)$alkoxy-, halo$(C_1-C_4)$alkoxy$(C_2-C_6)$alkoxy-, or hydroxy$(C_2-C_6)$alkoxy-.

In one embodiment, $R^2$ is chloro, —OH, —$OCH_3$, —$OCF_2H$, —$OCH(CH_3)_2$, —$OCH_2CH_3$, —$OCH_2CF_3$, —$OCH_2CH_2CH_3$, —$OCH_2CH_2OH$, —$OCH_2CH_2CH_2OH$, —$OCH_2CH_2OCH_3$, —$OC(CH_3)_2CH_2OH$, —$OCH(CH_3)CH_2OH$, —$OCH_2CH(CH_3)OH$, —$OCH_2$-cyclohexyl, or —O-tetrahydro-2H-pyran-4-yl.

In yet another embodiment, $R^2$ is fluoro or $R^2$ is —$OCF_3$, —$OCF_2H$, —$OCH_2CHF_2$, —$OCH_2C(CH_3)_2OH$, —$OCH_2C(CH_3)_3$, —$OCH_2CH(CH_3)OH$, or —$OCH_2CH_2OCF_3$.

In yet another embodiment, $R^2$ is —$OCH_2$-cyclopropyl, —$OCH_2$-tetrahydrofuran-2-yl, —$OCH_2$-tetrahydrofuran-3-yl, —$OCH_2$-tetrahydro-2H-pyran-2-yl, —$OCH_2$-tetrahydro-2H-pyran-3-yl, —$OCH_2$-tetrahydro-2H-pyran-4-yl, or —$OCH_2$-oxiran-3-yl.

In another embodiment, $R^2$ is fluoro or $R^2$ is —$OCF_3$, —$OCF_2H$, —$OCH_2CHF_2$, —$OCH_2CF_3$, —$OCH_2C(CH_3)_2OH$, —$OCH_2CH(CH_3)OH$, —$OCH_2CH_2OCH_3$, —$OCH_2CH_2OCH_3$ or —$OCH_2CH_2OCF_3$. In yet another embodiment, $R^2$ is —$OCH_2C(CH_3)_2OH$, —$OCH_2CH(CH_3)OH$ or —$OCH_2CH_2OCH_3$.

In another embodiment of the compounds of this invention, $R^3$ is H or methyl, $R^4$ is methyl or trifluoromethyl, and $R^5$ is H or methyl. In a further embodiment, $R^3$, $R^4$, and $R^5$ are each methyl. In a further embodiment, $R^3$ and $R^4$ are both methyl, and $R^5$ is H.

Representative compounds of the invention include the compounds of Examples 1-10.

In another embodiment, a compound of the invention is selected from:
1-((6-(tert-butylsulfonyl)-4-((3,4-dimethyl-1H-pyrazol-5-yl)amino)quinolin-7-yl)oxy)propan-2-ol,
(R)-1-((6-(tert-butylsulfonyl)-4-((3,4-dimethyl-1H-pyrazol-5-yl)amino)quinolin-7-yl)oxy)propan-2-ol,
(S)-1-((6-(tert-butylsulfonyl)-4-((3,4-dimethyl-1H-pyrazol-5-yl)amino)quinolin-7-yl)oxy)propan-2-ol, 1-((6-(tert-butylsulfonyl)-4-((3,4-dimethyl-1H-pyrazol-5-yl)amino)quinolin-7-yl)oxy)-2-methylpropan-2-ol,
6-(tert-butylsulfonyl)-7-(2,2-difluoroethoxy)-N-(3,4-dimethyl-1H-pyrazol-5-yl)quinolin-4-amine,
6-(tert-butylsulfonyl)-N-(3,4-dimethyl-1H-pyrazol-5-yl)-7-(3-methoxypropoxy)quinolin-4-amine,
6-(tert-butylsulfonyl)-N-(4,5-dimethyl-1H-pyrazol-3-yl)-7-(2,2,2-trifluoroethoxy)quinolin-4-amine,
6-(tert-butylsulfonyl)-N-(3,4-dimethyl-1H-pyrazol-5-yl)-7-(2-methoxyethoxy)quinolin-4-amine, and
6-(tert-butylsulfonyl)-N-(3,4-dimethyl-1H-pyrazol-5-yl)-7-fluoroquinolin-4-amine,
or a salt thereof, particularly a pharmaceutically acceptable salt thereof.

In another embodiment representative compounds of the invention include the following compounds:
1-((6-(tert-butylsulfonyl)-4-((3,4-dimethyl-1H-pyrazol-5-yl)amino)quinolin-7-yl)oxy)propan-2-ol;
1-((6-(tert-butylsulfonyl)-4-((3,4-dimethyl-1H-pyrazol-5-yl)amino)quinolin-7-yl)oxy)-2-methylpropan-2-ol;
6-(tert-butylsulfonyl)-7-(2,2-difluoroethoxy)-N-(3,4-dimethyl-1H-pyrazol-5-yl)quinolin-4-amine;
6-(tert-butylsulfonyl)-N-(3,4-dimethyl-1H-pyrazol-5-yl)-7-(3-methoxypropoxy)quinolin-4-amine;
6-(tert-butylsulfonyl)-N-(4,5-dimethyl-1H-pyrazol-3-yl)-7-(2-methoxyethoxy)quinolin-4-amine;
6-(tert-butylsulfonyl)-N-(4,5-dimethyl-1H-pyrazol-3-yl)-7-(2,2,2-trifluoroethoxy)quinolin-4-amine;
6-(tert-butylsulfonyl)-N-(3,4-dimethyl-1H-pyrazol-5-yl)-7-fluoroquinolin-4-amine;
or a salt thereof, particularly a pharmaceutically acceptable salt thereof.

It will be appreciated that the present invention encompasses compounds of Formula (I) as the free base and as salts thereof, for example as a pharmaceutically acceptable salt thereof. In one embodiment the invention relates to compounds of Formula (I) in the form of a free base. In another embodiment the invention relates to compounds of Formula (I) or a pharmaceutically acceptable salt thereof. It will further be appreciated that compounds of Formula (I) and salts thereof may exist in hydrated form, such as the monohydrate.

A particular compound of the invention is 1-((6-(tert-butylsulfonyl)-4-((3,4-dimethyl-1H-pyrazol-5-yl)amino)quinolin-7-yl)oxy)propan-2-ol as the free base. In another embodiment, the compound of the invention is 1-((6-(tert-butylsulfonyl)-4-((3,4-dimethyl-1H-pyrazol-5-yl)amino)quinolin-7-yl)oxy)propan-2-ol or a salt thereof. In another embodiment, the compound of the invention is 1-((6-(tert-butylsulfonyl)-4-((3,4-dimethyl-1H-pyrazol-5-yl)amino)quinolin-7-yl)oxy)propan-2-ol or a pharmaceutically acceptable salt thereof.

In another embodiment, the compound of the invention is (R)-1-((6-(tert-butylsulfonyl)-4-((3,4-dimethyl-1H-pyrazol-5-yl)amino)quinolin-7-yl)oxy)propan-2-ol or (S)-1-((6-(tert-butylsulfonyl)-4-((3,4-dimethyl-1H-pyrazol-5-yl)amino)quinolin-7-yl)oxy)propan-2-ol as the free base. In another embodiment, the compound of the invention is (R)-1-((6-(tert-butylsulfonyl)-4-((3,4-dimethyl-1H-pyrazol-5-yl)amino)quinolin-7-yl)oxy)propan-2-ol or (S)-1-((6-(tert-butylsulfonyl)-4-((3,4-dimethyl-1H-pyrazol-5-yl)amino)quinolin-7-yl)oxy)propan-2-ol or a salt thereof. In another embodiment, the compound of the invention is (R)-1-((6-(tert-butylsulfonyl)-4-((3,4-dimethyl-1H-pyrazol-5-yl)amino)quinolin-7-yl)oxy)propan-2-ol or (S)-1-((6-(tert-butylsulfonyl)-4-((3,4-dimethyl-1H-pyrazol-5-yl)amino)quinolin-7-yl)oxy)propan-2-ol or a pharmaceutically acceptable salt thereof.

A particular compound of the invention is (R)-1-((6-(tert-butylsulfonyl)-4-((3,4-dimethyl-1H-pyrazol-5-yl)amino)quinolin-7-yl)oxy)propan-2-ol as the free base. One specific embodiment of the invention is the compound (R)-1-((6-(tert-butylsulfonyl)-4-((3,4-dimethyl-1H-pyrazol-5-yl)amino)quinolin-7-yl)oxy)propan-2-ol or a salt thereof. Another specific embodiment of the invention is the compound (R)-1-((6-(tert-butylsulfonyl)-4-((3,4-dimethyl-1H-pyrazol-5-yl)amino)quinolin-7-yl)oxy)propan-2-ol or a pharmaceutically acceptable salt thereof. One specific embodiment of the invention is the compound (R)-1-((6-(tert-butylsulfonyl)-4-((3,4-dimethyl-1H-pyrazol-5-yl)amino)quinolin-7-yl)oxy)propan-2-ol, hydrochloride. A further specific embodiment of the invention is the compound (R)-1-((6-(tert-butylsulfonyl)-4-((3,4-dimethyl-1H-pyrazol-5-yl)amino)quinolin-7-yl)oxy)propan-2-ol, hydrochloride having the PXRD of FIG. 1.

Another particular compound of the invention is 1-((6-(tert-butylsulfonyl)-4-((3,4-dimethyl-1H-pyrazol-5-yl)amino)quinolin-7-yl)oxy)-2-methylpropan-2-ol as the free base. One specific embodiment of the invention is the compound 1-((6-(tert-butylsulfonyl)-4-((3,4-dimethyl-1H-pyrazol-5-yl)amino)quinolin-7-yl)oxy)-2-methylpropan-2-ol or a salt thereof. Another specific embodiment of the invention is the compound 1-((6-(tert-butylsulfonyl)-4-((3,4-dimethyl-1H-pyrazol-5-yl)amino)quinolin-7-yl)oxy)-2-methylpropan-2-ol or a pharmaceutically acceptable salt thereof.

Figure 2:
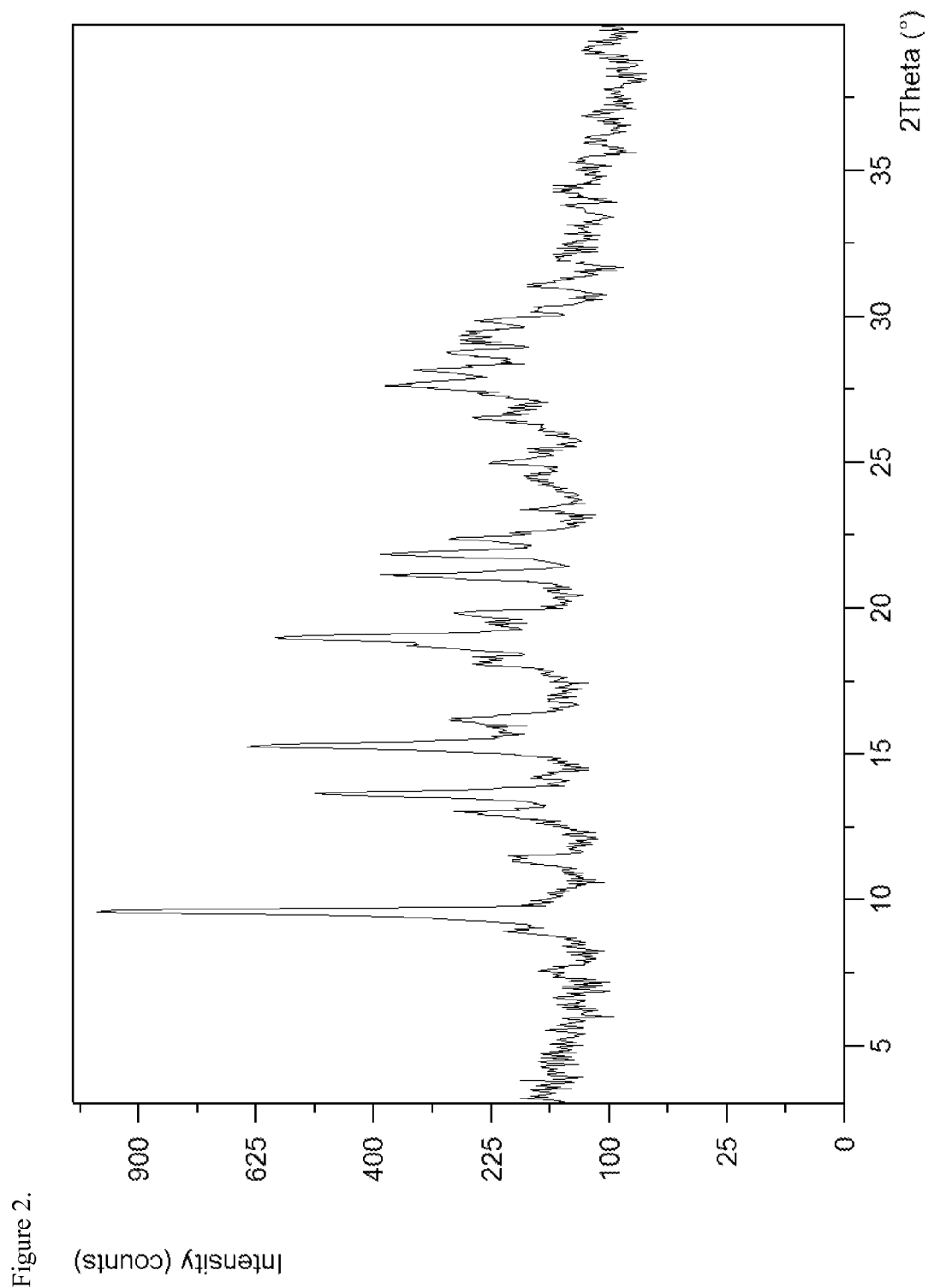
FIG. 2 is a PXRD pattern of a crystalline form of 6-(tert-butylsulfonyl)-N-(4,5-dimethyl-1H-pyrazol-3-yl)-7-(2-methoxyethoxy)quinolin-4-amine, hydrochloride, monohydrate.

Another particular compound of the invention is 6-(tert-butylsulfonyl)-N-(3,4-dimethyl-1H-pyrazol-5-yl)-7-(2-methoxyethoxy)quinolin-4-amine as the free base. One specific embodiment of the invention is the compound 6-(tert-butylsulfonyl)-N-(3,4-dimethyl-1H-pyrazol-5-yl)-7-(2-methoxyethoxy)quinolin-4-amine, or a salt thereof. Another specific embodiment of the invention is the compound 6-(tert-butylsulfonyl)-N-(3,4-dimethyl-1H-pyrazol-5-yl)-7-(2-methoxyethoxy)quinolin-4-amine, or a pharmaceutically acceptable salt thereof. Another specific embodiment of the invention is the compound 6-(tert-butylsulfonyl)-N-(3,4-dimethyl-1H-pyrazol-5-yl)-7-(2-methoxyethoxy)quinolin-4-amine, hydrochloride. Another specific embodiment of a compound of the invention is 6-(tert-butylsulfonyl)-N-(4,5-dimethyl-1H-pyrazol-3-yl)-7-(2-methoxyethoxy)quinolin-4-amine, hydrochloride, monohydrate. A further specific embodiment of a compound of the invention is 6-(tert-butylsulfonyl)-N-(4,5-dimethyl-1H-pyrazol-3-yl)-7-(2-methoxyethoxy)quinolin-4-amine, hydrochloride, monohydrate having the PXRD of FIG. 2.

Accordingly, a compound of the invention includes a compound of Formula (I), or a salt thereof, particularly a pharmaceutically acceptable salt thereof. Specifically, a compound of the invention includes a compound of Formula (I), particularly the specific compounds described herein, or a salt thereof, particularly a pharmaceutically acceptable salt thereof.

In one embodiment, the invention is directed to a method of inhibiting RIP2 kinase comprising contacting a cell with a compound of the invention. In another embodiment, the invention is directed to a method of treating a RIP2 kinase-mediated disease or disorder comprising administering a therapeutically effective amount of a compound of the invention to a human in need thereof.

This invention is directed to a method of treating a disease or disorder mediated by inhibition of RIP2 kinase comprising administering a therapeutically effective amount of a compound of the invention to a human in need thereof. This invention is also directed to a method of treating a disease or disorder mediated by inhibition of RIP2 kinase comprising administering a therapeutically effective amount of the compound according to Formula (I) or a pharmaceutically acceptable salt thereof, to a human in need thereof.

The invention is still further directed to the use of a compound of the invention or a pharmaceutical composition comprising a compound of the invention to inhibit RIP2 kinase and/or treat a RIP2 kinase-mediated disease or disorder.

The compounds according to Formula (I) may contain one or more asymmetric center (also referred to as a chiral center) and may, therefore, exist as individual enantiomers, diastereomers, or other stereoisomeric forms, or as mixtures thereof. Chiral centers, such as a chiral carbon, may also be present in the compounds of this invention. Where the stereochemistry of a chiral center present in a compound of this invention (e.g., compound name) or in any chemical structure illustrated herein is not specified, the compound, compound name, or structure is intended to encompass all individual stereoisomers and all mixtures thereof. Thus, compounds according to Formula (I) containing one or more chiral center may be present as racemic mixtures, enantiomerically enriched mixtures, or as enantiomerically pure individual stereoisomers. It will be appreciated from the foregoing that the use of the compound name 1-((6-(tert-butylsulfonyl)-4-((3,4-dimethyl-1H-pyrazol-5-yl)amino)quinolin-7-yl)oxy)propan-2-ol encompasses all individual stereoisomers and mixtures thereof.

Individual stereoisomers of a compound according to Formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

It is to be understood that a solid form of a compound of the invention may exist in crystalline forms, non-crystalline forms or a mixture thereof. Such crystalline forms may also exhibit polymorphism (i.e. the capacity to occur in different crystalline forms). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

When a compound of the invention (I) is a base (contains a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like, or with a pyranosidyl acid, such as glucuronic acid or galacturonic acid, or with an alpha-hydroxy acid, such as citric acid or tartaric acid, or with an amino acid, such as aspartic acid or glutamic acid, or with an aromatic acid, such as benzoic acid or cinnamic acid, or with a sulfonic acid, such as p-toluenesulfonic acid, methanesulfonic acid, ethanesulfonic acid or the like.

Suitable addition salts include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfite, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, dinitrobenzoate, hydroxybenzoate, methoxybenzoate, phthalate, phenylacetate, phenylpropionate, phenylbutrate, lactate, γ-hydroxybutyrate, mandelate, and sulfonates, such as xylenesulfonate, propanesulfonate, naphthalene-1-sulfonate and naphthalene-2-sulfonate.

If a basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as N-methyl-D-glucamine, diethylamine, isopropylamine, trimethylamine, ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Because of their potential use in medicine, the salts of the compounds of Formula (I) are preferably pharmaceutically acceptable salts. Suitable pharmaceutically acceptable salts include acid or base addition salts, such as those described by Berge, Bighley and Monkhouse J. Pharm. Sci (1977) 66, pp 1-19 and "Pharmaceutical Salts: Properties, Selection, and Use, 2nd Revised Edition," P. H. Stahl and C. G. Wermuth (eds.), Wiley, Hoboken, N.J., US (2011). The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Pharmaceutically acceptable salt(s)" refers to a compound which is suitable for pharmaceutical use. Salt and solvate (e.g. hydrates and hydrates of salts) forms of the compounds of Formula (I) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their salts and solvates.

Examples of pharmaceutically acceptable acid-addition salts include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride, hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate, diphosphate, proprionate, pyroglutamate, salicylate, sebacate, stearate, succinate, sulfate, tartrate, thiocyanate, tosylate, undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate. In one embodiment the pharmaceutically acceptable acid-addition salt is hydrochloride. Non-pharmaceutically acceptable salts, e.g. trifluoroacetate, may be used, for example in the isolation of a compound of Formula (I), and are included within the scope of this invention.

Examples of pharmaceutically acceptable base-addition salts include ammonium, lithium, sodium, potassium, calcium, magnesium, aluminum salts, zinc salts, trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, glucamine, N-methylglucamine, collidine, quinine, quinoline, lysine and arginine.

Certain of the compounds of the invention may form salts with one or more equivalents of an acid (if the compound contains a basic moiety) or a base (if the compound contains an acidic moiety). The present invention includes within its scope all possible stoichiometric and non-stoichiometric salt forms.

Compounds of the invention having both a basic and acidic moiety may be in the form of zwitterions, acid-addition salt of the basic moiety or base salts of the acidic moiety.

This invention also provides for the conversion of one pharmaceutically acceptable salt of a compound of this invention into another pharmaceutically acceptable salt of a compound of this invention.

If a basic compound is isolated as a salt, the corresponding free acid or free base form of that compound may be prepared by any suitable method known to the art. For solvates of the compounds of Formula (I), including solvates of salts of the compounds of Formula (I), that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates, particularly hydrates, for example the monohydrate. Thus the invention provides a compound of Formula (I) or a salt thereof, especially a pharmaceutically acceptable salt thereof, as a solvate, particularly as a hydrate, such as a monohydrate.

Because the compounds of Formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

General Synthetic Methods

The compounds of Formula (I) may be obtained by using synthetic procedures illustrated in the Schemes below or by drawing on the knowledge of a skilled organic chemist. The syntheses provided in these Schemes are applicable for producing compounds of the invention having a variety of different substituent groups employing appropriate precursors, which are suitably protected if needed, to achieve compatibility with the reactions outlined herein. Subsequent deprotection, where needed, affords compounds of the nature generally disclosed. While the Schemes are shown with compounds only of Formula (I), they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

Scheme 1: 6-bromo-4-chloro-7-(methyloxy)quinolines may be synthesized via condensation of an aniline with Meldrum's acid followed by cyclization to the hydroxyquinoline. Conversion of the hydroxyquinoline to the chloroquinoline may be achieved with $POCl_3$.

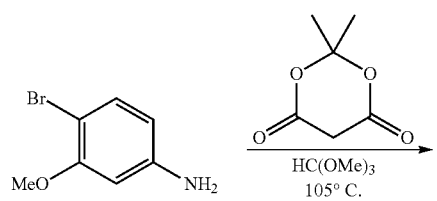

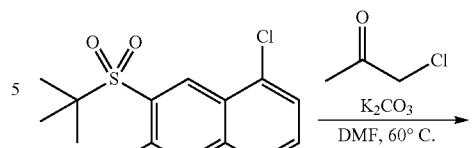

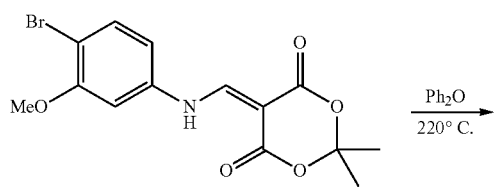

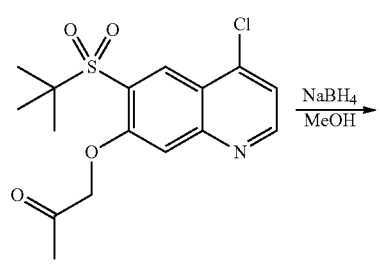

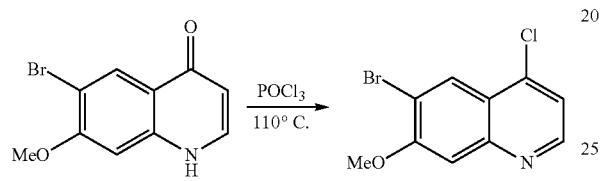

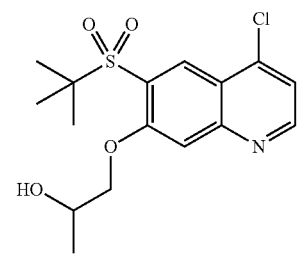

Scheme 2: 6-(tert-butylsulfonyl)-4-chloroquinolin-7-ols may be synthesized via palladium-catalyzed substitution of the aryl bromide followed by oxone-mediated oxidation of the thioether to the sulfone and subsequent demethylation with LiI.

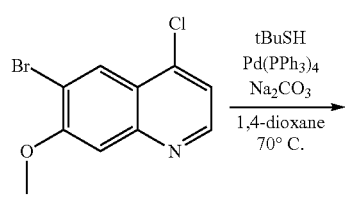

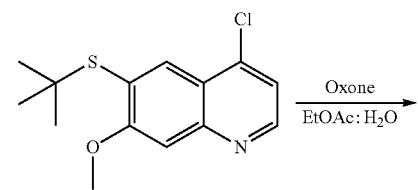

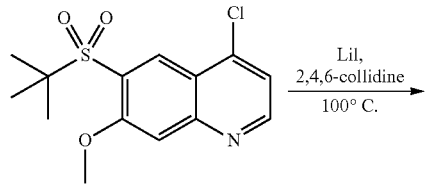

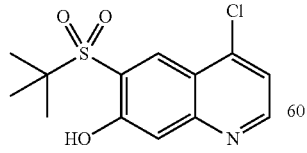

Scheme 3: 1-((6-(tert-butylsulfonyl)-4-chloroquinolin-7-yl)oxy)propan-2-ols may be made via alkylation of the 7-quinolinol with chloroacetone and subsequent reduction with sodium borohydride.

Scheme 4: Substituent "Z" groups may be appended to quinoline core after "$R^a$" is fixed by treatment of the chloroquinoline core with the appropriate aromatic amine in ethanol at elevated temperature mediated by catalytic HCl. N-methylpyrrolidinone may also be used as solvent for this reaction under neutral conditions (no HCl) at 100° C.

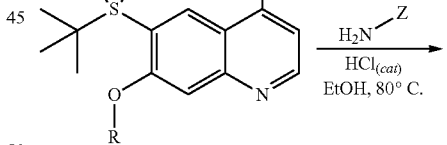

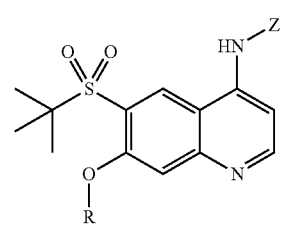

Scheme 5: Substituent "$R^a$" may be added to the 7-quinolinol through alkylation of electrophiles such as alkyl halides or epoxides under the action of base, generally NaH, K$_2$CO$_3$, or KOtBu, with or without a catalyst (such as NaI), in solvents such as DMF or acetonitrile at temperatures ranging from 0° C.-100° C. This reaction can also be done through Mitsunobu displacement through hydroxyalkyl group.

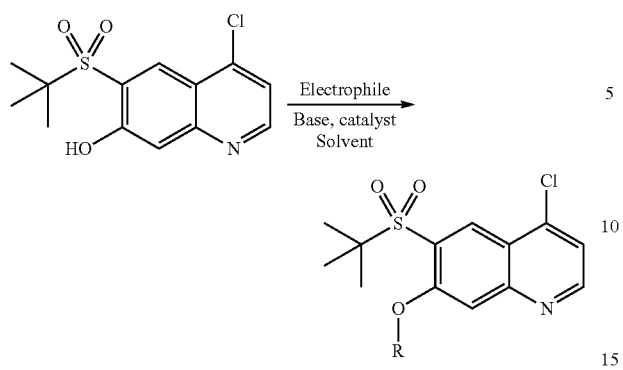
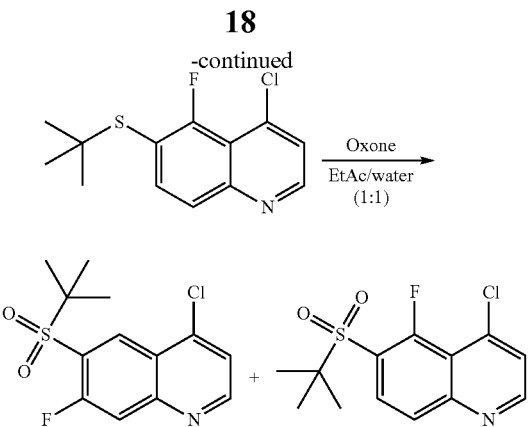

Scheme 6: 6-(tert-butylthio)-4-chloro-7-fluoroquinoline/6-(tert-butylthio)-4-chloro-5-fluoroquinolines may be synthesized via the condensation of 4-bromo-3-fluoroaniline with Meldrum's acid followed by cyclization to the 5- and 7-isomers of the fluoroquinolones. These isomers can be chlorinated with POCl$_3$, with subsequent palladium catalyzed thioether formation and oxidation to the sulfone with oxone. The final 6-(tert-butylthio)-4-chloro-7-fluoroquinoline and 6-(tert-butylthio)-4-chloro-5-fluoroquinolines are separable by normal phase column chromatography.

The compounds of the invention may be particularly useful for treatment of RIP2 kinase-mediated diseases or disorders, particularly diseases or disorders mediated by inhibition of RIP2 kinase, such as uveitis, interleukin-1 converting enzyme (ICE, also known as Caspase-1) associated fever syndrome (ICE fever), dermatitis, acute lung injury, type 2 diabetes mellitus, arthritis (specifically rheumatoid arthritis), inflammatory bowel disorders (such as ulcerative colitis and Crohn's disease), early-onset inflammatory bowel disease, extraintestinal inflammatory bowel disease, prevention of ischemia reperfusion injury in solid organs (specifically kidney) in response ischemia induced by cardiac surgery, organ transplant, sepsis and other insults, liver diseases (non-alcohol steatohepatitis, alcohol steatohepatitis, and autoimmune hepatitis), allergic diseases (such as asthma), transplant reactions (such as graft versus host disease), autoimmune diseases (such as systemic lupus erythematosus, and multiple sclerosis), and granulomateous disorders (such as sarcoidosis, Blau syndrome, early-onset sarcoidosis, Wegner's granulomatosis, and interstitial pulmonary disease).

The compounds of this invention may be particularly useful in the treatment of uveitis, ICE fever, Blau Syndrome, early-onset sarcoidosis, ulcerative colitis, Crohn's disease, Wegener's granulamatosis and sarcoidosis.

In one embodiment the invention is directed to a method of treating uveitis comprising administering a therapeutically effective amount of the compound according to Formula (I) or a pharmaceutically acceptable salt thereof, to a human in need thereof. In another embodiment the invention is directed to a method of treating interleukin-1 converting enzyme associated fever syndrome comprising administering a therapeutically effective amount of the compound according to Formula (I) or a pharmaceutically acceptable salt thereof, to a human in need thereof. In another embodiment the invention is directed to a method of treating Blau syndrome comprising administering a therapeutically effective amount of the compound according to Formula (I) or a pharmaceutically acceptable salt thereof, to a human in need thereof. In another embodiment the invention is directed to a method of treating early-onset sarcoidosis comprising administering a therapeutically effective amount of the compound according to Formula (I) or a pharmaceutically acceptable salt thereof, to a human in need thereof. In another embodiment the invention is directed to a method of treating ulcerative colitis comprising administering a therapeutically effective amount of the compound according to Formula (I) or a pharmaceutically acceptable salt thereof, to a human in need thereof. In another embodiment the invention is directed to a method of treating Crohn's disease comprising administering a therapeutically effective amount of the compound according to Formula (I) or a pharmaceutically acceptable salt thereof, to a human in need thereof. In another embodiment the invention is directed to a method of treating Wegner's Granulomatosis comprising administering a therapeutically effective amount of the compound according to Formula (I) or a pharmaceutically acceptable salt thereof, to a human in need thereof. In a further embodiment the invention is directed to a method of treating sarcoidosis comprising administering a therapeutically effective amount of the compound according to Formula (I) or a pharmaceutically acceptable salt thereof, to a human in need thereof.

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, particularly for the treatment of refractory cases, such as in combination with other anti-inflammatory and/or anti-TNF agents, which may be administered in therapeutically effective amounts as is known in the art.

The compounds of Formula (I) and pharmaceutically acceptable salts thereof may be employed alone or in combination with other therapeutic agents. Combination therapies according to the present invention thus comprise the administration of at least one compound of Formula (I) or a pharmaceutically acceptable salt thereof, and the use of at least one other therapeutically active agent. Preferably, combination therapies according to the present invention comprise the administration of at least one compound of Formula (I) or a pharmaceutically acceptable salt thereof, and at least one other therapeutically active agent. The compound(s) of Formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of Formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of Formula (I) or a pharmaceutically acceptable salt thereof, together with one or more other therapeutically active agents.

Thus in one aspect, the compound of Formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example an anti-inflammatory agent and/or an anti-TNF agent.

The compounds of the invention may be administered in combination with corticosteroids and/or anti-TNF agents to treat Blau syndrome, early-onset sarcoidosis; or in combination with anti-TNF biologics or other anti-inflammatory biologics to treat Crohn's Disease; or in combination with 5-ASA (mesalamine) or sulfasalazine to treat ulcerative colitis; or in combination with low-dose corticosteroids and/or methotrexate to treat Wegener's granulamatosis or sarcoidosis or interstitial pulmonary disease; or in combination with a biologic (e.g. anti-TNF, anti-IL-6, etc.) to treat rheumatoid arthritis; or in combination with anti-IL6 and/or methotrexate to treat ICE fever.

Examples of suitable anti-inflammatory agents include 5-aminosalicyclic acid and mesalamine preparations, sulfasalazine, hydroxycloroquine, thiopurines (azathioprin, mercaptopurin), methotrexate, cyclophosphamide, cyclosporine, JAK inhibitors (tofacitinib), corticosteroids, particularly low-dose corticosteroids (such as prednisone (Deltasone®) and bundesonide) and anti-inflammatory biologics such as anti-IL6R mAbs (Actemra® (tocilizumab)), anti-IL6 biologics, anti-IL1 or IL12 or IL23 biologics (ustekinumab (Stelara®)), anti-integrin agents (natalizumab (Tysabri®)), anti-CD20 mAbs (rituximab (Rituxan®) and ofatumumab (Arzerra®)), and other agents, such as abatacept (Orencia®), anakinra (Kineret®), and belimumab (Benlysta®), CD4 biologics and other cytokine inhibitors or biologics to T-cell or B-cell receptors or interleukins. Examples of suitable anti-TNF agents include the anti-TNF biologics such as Enbrel® (etanecerpt), Humira® (adalimumab), Remicade® (infliximab), Cimzia® (certolizumab), and Simponi® (golimumab).

This invention provides a compound of the invention for use in therapy. This invention also provides a compound of Formula (I), or a pharmaceutically acceptable salt thereof, for use in therapy. Specifically, this invention provides the compounds described herein for use in therapy.

In another embodiment, this invention provides a compound of the invention for use in the treatment of a disease or disorder mediated by inhibition of RIP2 kinase. In another embodiment, this invention provides a compound of Formula (I), or a pharmaceutically acceptable salt thereof, for use in the treatment of a disease or disorder mediated by inhibition of RIP2 kinase. Specifically, this invention provides the compounds described herein for use in the treatment of a disease or disorder mediated by inhibition of RIP2 kinase. In another embodiment this invention provides a compound of Formula (I), or a pharmaceutically acceptable salt thereof, for use in the treatment of uveitis, interleukin-1 converting enzyme associated fever syndrome, dermatitis, acute lung injury, type 2 diabetes mellitus, arthritis, rheumatoid arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, alcohol steatohepatitis, autoimmune hepatitis, asthma, graft versus host disease, systemic lupus erythematosus, multiple sclerosis, sarcoidosis, Blau syndrome/early-onset sarcoidosis, Wegner's granulomatosis or interstitial pulmonary disease. In another embodiment this invention provides a compound of Formula (I), or a pharmaceutically acceptable salt thereof, for use in the treatment of uveitis. In another embodiment this invention provides a compound of Formula (I), or a pharmaceutically acceptable salt thereof, for use in the treatment of interleukin-1 converting enzyme associated fever syndrome. In another embodiment this invention provides a compound of Formula (I), or a pharmaceutically acceptable salt thereof, for use in the treatment of Blau syndrome. In another embodiment this invention provides a compound of Formula (I), or a pharmaceutically acceptable salt thereof, for use in the treatment of early-onset sarcoidosis. In another embodiment this invention provides a compound of Formula (I), or a pharmaceutically acceptable salt thereof, for use in the treatment of ulcerative colitis. In another embodiment this invention provides a compound of Formula (I), or a pharmaceutically acceptable salt thereof, for use in the treatment of Crohn's disease. In another embodiment this invention provides a compound of Formula (I), or a pharmaceutically acceptable salt thereof, for use in the treatment of early-onset inflammatory bowel disease. In another embodiment this invention provides a compound of Formula (I), or a pharmaceutically acceptable salt thereof, for use in the treatment of extraintestinal inflammatory bowel disease. In another embodiment this invention provides a compound of Formula (I), or a pharmaceutically acceptable salt thereof, for use in the treatment of Wegner's Granulomatosis. In another embodiment this invention provides a compound of Formula (I), or a pharmaceutically acceptable salt thereof, for use in the treatment of sarcoidosis.

This invention specifically provides for the use of a compound of Formula (I), or a pharmaceutically acceptable salt thereof, as an active therapeutic substance in the treatment of a RIP2 kinase-mediated disease or disorder, for example the diseases and disorders recited herein. More specifically, this invention provides for the use of a compound of Formula (I), or a pharmaceutically acceptable salt thereof, for the treatment of a disease or disorder mediated by inhibition of RIP2 kinase. This invention specifically provides for the use of the compounds described herein for the treatment of a disease or disorder mediated by inhibition of RIP2 kinase. Accordingly, the invention provides for the use of a compound of Formula (I), or a pharmaceutically acceptable salt thereof, as an active therapeutic substance in the treatment of a human in need thereof with a disease mediated by inhibition of RIP2 kinase.

The invention also provides for the use of a compound of Formula (I), or a pharmaceutically acceptable salt thereof, in the manufacture of a medicament for use in the treatment of a RIP2 kinase-mediated disease or disorder, for example the diseases and disorders recited herein. More specifically, this invention provides for the use of a compound of Formula (I), or a pharmaceutically acceptable salt thereof, in the manufacture of a medicament for the treatment of a disease or disorder mediated by inhibition of RIP2 kinase. Accordingly, the invention provides for the use of a compound of Formula (I), or a pharmaceutically acceptable salt thereof, in the manufacture of a medicament for use in the treatment of a human in need thereof with a disease or disorder mediated by inhibition of RIP2 kinase. In one embodiment this invention provides for the use of a compound of Formula (I), or a pharmaceutically acceptable salt thereof, in the manufacture of a medicament for use in the treatment of uveitis, interleukin-1 converting enzyme associated fever syndrome, dermatitis, acute lung injury, type 2 diabetes mellitus, arthritis, rheumatoid arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, alcohol steatohepatitis, autoimmune hepatitis, asthma, graft versus host disease, systemic lupus erythematosus, multiple sclerosis, sarcoidosis, Blau syndrome/early-onset sarcoidosis, Wegner's granulomatosis or interstitial pulmonary disease. In another embodiment this invention provides for the use of a compound of Formula (I), or a pharmaceutically acceptable salt thereof, in the manufacture of a medicament for use in the treatment of uveitis. In another embodiment this invention provides for the use of a compound of Formula (I), or a pharmaceutically acceptable salt thereof, in the manufacture of a medicament for use in the treatment of interleukin-1 converting enzyme associated fever syndrome. In another embodiment this invention provides for the use of a compound of Formula (I), or a pharmaceutically acceptable salt thereof, in the manufacture of a medicament for use in the treatment of early-onset sarcoidosis. In another embodiment this invention provides for the use of a compound of Formula (I), or a pharmaceutically acceptable salt thereof, in the manufacture of a medicament for use in the treatment of ulcerative colitis. In another embodiment this invention provides for the use of a compound of Formula (I), or a pharmaceutically acceptable salt thereof, in the manufacture of a medicament for use in the treatment of Crohn's disease. In another embodiment this invention provides for the use of a compound of Formula (I), or a pharmaceutically acceptable salt thereof, in the manufacture of a medicament for use in the treatment of Wegner's Granulomatosis. In another embodiment this invention provides for the use of a compound of Formula (I), or a pharmaceutically acceptable salt thereof, in the manufacture of a medicament for use in the treatment of sarcoidosis. In another embodiment this invention provides for the use of a compound of Formula (I), or a pharmaceutically acceptable salt thereof, in the manufacture of a medicament for use in the treatment of early-onset inflammatory bowel disease. In another embodiment this invention provides for the use of a compound of Formula (I), or a pharmaceutically acceptable salt thereof, in the manufacture of a medicament for use in the treatment of extraintestinal inflammatory bowel disease. In a further embodiment this invention provides for the use of a compound of Formula (I), or a pharmaceutically acceptable salt thereof, in the manufacture of a medicament for use in the treatment of Blau syndrome.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate or inhibit the activity of RIP2 kinase such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for prevention, retardation, prophylaxis, therapy or cure of a mediated disease or disorder. Specific diseases and disorders that may be particularly susceptible to treatment using a compound of this invention are described herein.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

For use in therapy, the compounds of the invention will be normally, but not necessarily, formulated into a pharmaceutical composition prior to administration to a patient. Accordingly, the invention also is directed to pharmaceutical compositions comprising a compound of the invention and one or more pharmaceutically acceptable excipients.

In one embodiment, there is provided a pharmaceutical composition comprising 1-((6-(tert-butylsulfonyl)-4-((3,4-dimethyl-1H-pyrazol-5-yl)amino)quinolin-7-yl)oxy)propan-2-ol as the free base and one or more pharmaceutically acceptable excipients. In another embodiment, there is provided a pharmaceutical composition comprising 1-((6-(tert-butylsulfonyl)-4-((3,4-dimethyl-1H-pyrazol-5-yl)amino)quinolin-7-yl)oxy)propan-2-ol or a pharmaceutically acceptable salt thereof and one or more pharmaceutically acceptable excipients.

In another embodiment, there is provided a pharmaceutical composition comprising (R)-1-((6-(tert-butylsulfonyl)-4-((3,4-dimethyl-1H-pyrazol-5-yl)amino)quinolin-7-yl)oxy)propan-2-ol or (S)-1-((6-(tert-butylsulfonyl)-4-((3,4-dimethyl-1H-pyrazol-5-yl)amino)quinolin-7-yl)oxy)propan-2-ol as the free base and one or more pharmaceutically acceptable excipients. In another embodiment, there is provided a pharmaceutical composition comprising (R)-1-((6-(tert-butylsulfonyl)-4-((3,4-dimethyl-1H-pyrazol-5-yl)amino)quinolin-7-yl)oxy)propan-2-ol or (S)-1-((6-(tert-butylsulfonyl)-4-((3,4-dimethyl-1H-pyrazol-5-yl)amino)quinolin-7-yl)oxy)propan-2-ol or a pharmaceutically acceptable salt thereof and one or more pharmaceutically acceptable excipients.

In another embodiment, there is provided a pharmaceutical composition comprising (R)-1-((6-(tert-butylsulfonyl)-4-((3,4-dimethyl-1H-pyrazol-5-yl)amino)quinolin-7-yl)oxy)propan-2-ol as the free base and one or more pharmaceutically acceptable excipients. In another embodiment, there is provided a pharmaceutical composition comprising (R)-1-((6-(tert-butylsulfonyl)-4-((3,4-dimethyl-1H-pyrazol-5-yl)amino)quinolin-7-yl)oxy)propan-2-ol or a pharmaceutically acceptable salt thereof and one or more pharmaceutically acceptable excipients. In another embodiment, there is provided a pharmaceutical composition comprising (R)-1-((6-(tert-butylsulfonyl)-4-((3,4-dimethyl-1H-pyrazol-5-yl)amino)quinolin-7-yl)oxy)propan-2-ol, hydrochloride and one or more pharmaceutically acceptable excipients. In another embodiment, there is provided a pharmaceutical composition comprising (R)-1-((6-(tert-butylsulfonyl)-4-((3,4-dimethyl-1H-pyrazol-5-yl)amino)quinolin-7-yl)oxy)propan-2-ol, hydrochloride having the PXRD of FIG. 1 and one or more pharmaceutically acceptable excipients.

In another embodiment, there is provided a pharmaceutical composition comprising 1-((6-(tert-butylsulfonyl)-4-((3,4-dimethyl-1H-pyrazol-5-yl)amino)quinolin-7-yl)oxy)-2-methylpropan-2-ol as the free base and one or more pharmaceutically acceptable excipients. In another embodiment, there is provided a pharmaceutical composition comprising 1-((6-(tert-butylsulfonyl)-4-((3,4-dimethyl-1H-pyrazol-5-yl)amino)quinolin-7-yl)oxy)-2-methylpropan-2-ol or a pharmaceutically acceptable salt thereof and one or more pharmaceutically acceptable excipients.

In another embodiment, there is provided a pharmaceutical composition comprising 6-(tert-butylsulfonyl)-N-(3,4-dimethyl-1H-pyrazol-5-yl)-7-(2-methoxyethoxy)quinolin-4-amine as the free base and one or more pharmaceutically acceptable excipients. In another embodiment, there is provided a pharmaceutical composition comprising 6-(tert-butylsulfonyl)-N-(3,4-dimethyl-1H-pyrazol-5-yl)-7-(2-methoxyethoxy)quinolin-4-amine, or a pharmaceutically acceptable salt thereof and one or more pharmaceutically acceptable excipients. In another embodiment, there is provided a pharmaceutical composition comprising 6-(tert-butylsulfonyl)-N-(3,4-dimethyl-1H-pyrazol-5-yl)-7-(2-methoxyethoxy)quinolin-4-amine, hydrochloride and one or more pharmaceutically acceptable excipients. In another embodiment, there is provided a pharmaceutical composition comprising 6-(tert-butylsulfonyl)-N-(4,5-dimethyl-1H-pyrazol-3-yl)-7-(2-methoxyethoxy)quinolin-4-amine, hydrochloride, monohydrate and one or more pharmaceutically acceptable excipients. In another embodiment, there is provided a pharmaceutical composition comprising 6-(tert-butylsulfonyl)-N-(4,5-dimethyl-1H-pyrazol-3-yl)-7-(2-methoxyethoxy)quinolin-4-amine, hydrochloride, monohydrate having the PXRD of FIG. 2 and one or more pharmaceutically acceptable excipients.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), or a salt, particularly a pharmaceutically acceptable salt, thereof). When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a RIP2 mediated disease or disorder.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I).

Names for the intermediate and final compounds described herein were generated using the software naming program ACD/Name Pro V6.02 available from Advanced Chemistry Development, Inc., 110 Yonge Street, 14$^{th}$ Floor, Toronto, Ontario, Canada, M5C 1T4 (http://www.acdlabs.com/) or the naming program in ChemDraw, Struct=Name Pro 12.0, as part of ChemBioDraw Ultra, available from CambridgeSoft. 100 CambridgePark Drive, Cambridge, Mass. 02140 USA (www.cambridgesoft.com). It will be appreciated by those skilled in the art that in certain instances this program will name a structurally depicted compound as a tautomer of that compound. It is to be understood that any reference to a named compound or a structurally depicted compound is intended to encompass all tautomers of such compounds and any mixtures of tautomers thereof.

In the following experimental descriptions, the following abbreviations may be used:

| Abbreviation | Meaning |
| --- | --- |
| 2-MeTHF | 2-methyl tetrahydrofuran |
| AcOH | acetic acid |
| aq | aqueous |
| brine | saturated aqueous NaCl |
| $CH_2Cl_2$, DCM | methylene chloride |
| $CH_3CN$ or MeCN or ACN | acetonitrile |

| Abbreviation | Meaning |
|---|---|
| $CH_3NH_2$ | methylamine |
| $Cs_2CO_3$ | cesium carbonate |
| conc. | concentrated |
| d | day |
| DCE | 1,2-dichloroethane |
| DMF | N,N-dimethylformamide |
| DMSO | dimethylsulfoxide |
| equiv | equivalents |
| Et | ethyl |
| $Et_2O$ or DME | diethyl ether |
| EtOAc | ethyl acetate |
| EtOH | ethanol |
| h, hr | hour |
| HCl | hydrochloric acid |
| IPA | isopropyl alcohol |
| $iPr_2O$ | diisopropyl ether |
| KOt-Bu | potassium tert-butoxide |
| $K_2CO_3$ | potassium carbonate |
| Me | methyl |
| MeOH or $CH_3OH$ | methanol |
| $MgSO_4$ | magnesium sulfate |
| min(s) | minute(s) |
| MS | mass spectrum |
| μw | microwave |
| $NaBH_4$ | sodium borohydride |
| $Na_2CO_3$ | sodium carbonate |
| $NaHCO_3$ | sodium bicarbonate |
| $Na_2SO_4$ | sodium sulfate |
| $NH_4Cl$ | ammonium chloride |
| NMP | N-methyl-2-pyrrolidone |
| $Pd_2dba_3$ | tris(dibenzylideneacetone)dipalladium(0) |
| Ph | phenyl |
| RBF or rbf | round bottomed flask |
| rt or RT | room temperature |
| satd or sat'd | Saturated |
| TFA | trifluoroacetic acid |
| THF | Tetrahydrofuran |
| $t_R$ | retention time |

Preparation 1

6-(tert-Butylsulfonyl)-4-chloroquinolin-7-ol

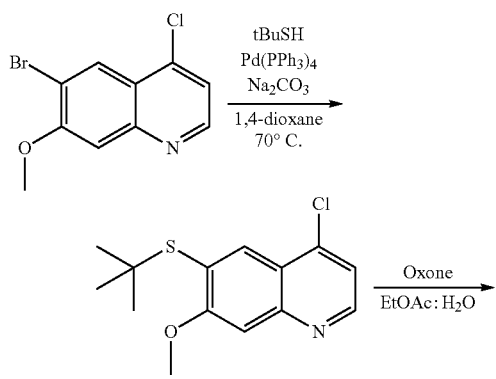

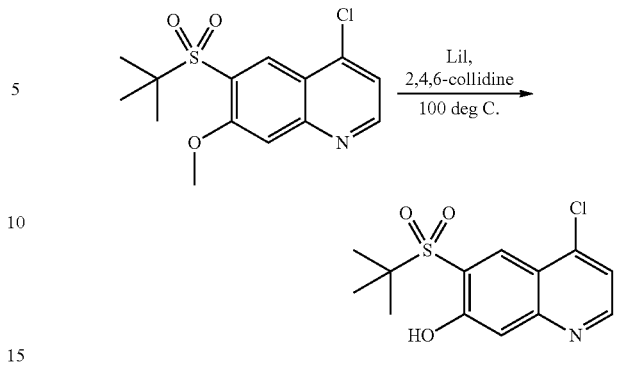

Step 1. 6-(tert-butylthio)-4-chloro-7-methoxyquinoline: A mixture of 6-bromo-4-chloro-7-methoxyquinoline (50 g, 183 mmol), $Pd(Ph_3P)_4$ (5.30 g, 4.59 mmol), $Na_2CO_3$ (48.6 g, 459 mmol) and 1,4-dioxane (895 mL) was purged with nitrogen for 10 minutes. 2-methyl-2-propanethiol (tBuSH; 22.75 mL, 202 mmol) was added and the reaction was heated at 70° C. for 4 d. The reaction was cooled to rt and flushed through a silica gel plug that had been pre-wetted with EtOAc using 100% EtOAc as the eluent. The product-containing fractions were triturated with MeOH and combined to afford 6-(tert-butylthio)-4-chloro-7-methoxyquinoline (37.5 g, 128 mmol, 69.6% yield). $^1$H NMR (400 MHz, DMSO-$d_6$) δ ppm 8.79 (d, J=4.8 Hz, 1H), 8.25 (s, 1H), 7.63 (d, J=4.8 Hz, 1H), 7.54 (s, 1H), 3.99 (s, 3H), 1.31 (s, 9H). MS (m/z) 282.

Step 2. 6-(tert-butylsulfonyl)-4-chloro-7-methoxyquinoline: To a solution of 6-(tert-butylthio)-4-chloro-7-methoxyquinoline (18.5 g, 63.0 mmol) in EtOAc (315 mL) and water (315 mL) was added oxone (44.6 g, 72.5 mmol). The reaction was stirred at rt for 18 h. The layers were separated and the aqueous layer was extracted twice with EtOAc. The combined organic extracts were concentrated to dryness, dissolved in a minimal amount of 10% MeOH/DCM, loaded onto a Biotage 340 g silica column and purified via column chromatography (Biotage SP-1, 340 g, 100% EtOAc for 20 min, then 0%-20% MeOH/EtOAc). The cleanest fractions were concentrated to dryness and triturated with EtOAc to provide 6-(tert-butylsulfonyl)-4-chloro-7-methoxyquinoline (15.2 g). $^1$H NMR (400 MHz, DMSO-$d_6$) δ ppm 8.95 (d, J=4.8 Hz, 1H), 8.65 (s, 1H), 7.71-7.79 (m, 2H), 4.04 (s, 3H), 1.31 (s, 9H). MS (m/z) 314.

Step 3. 6-(tert-butylsulfonyl)-4-chloroquinolin-7-ol: To an oven-dried rbf was added 6-(tert-butylsulfonyl)-4-chloro-7-methoxyquinoline (5.85 g, 18.64 mmol) followed by lithium iodide (7.49 g, 55.9 mmol) and 2,4,6-collidine (37.3 ml) This was heated to 100° C. for 4 hr. Diluted reaction with $iPr_2O$ with vigorous stirring and filtered resulting solid. When filtering though the Buchner funnel, rinsed with plenty of $iPr_2O$, keeping a layer of solvent over the filtercake so as not to expose to air. Then, very rapidly, completed the filtration and transferred the filtercake to a beaker. Diluted with 1N HCl (125 mL) and 2-MeTHF. Separated layers and extracted 4 times with 2-MeTHF and once with EtOAc. Washed combined organics with water then twice with 5% sodium thiosulfate (did these washes quickly so as not to promote any side reactions). Washed combined organics with brine, then dried on $MgSO_4$, filtered and concentrated to provide the product as a brown solid: 6-(tert-butylsulfonyl)-4-chloroquinolin-7-ol (5.07 g, 16.91 mmol, 91% yield). $^1$H NMR (400 MHz, DMSO-$d_6$) δ ppm 1.33 (s, 9H) 7.56 (s, 1H) 7.66 (d, J=4.80 Hz, 1H) 8.59 (s, 1H) 8.85 (d, J=4.80 Hz, 1H) 11.46 (s, 1H) MS: m/z: 300.0 [M+H]$^+$.

Example 1

1-((6-(tert-Butylsulfonyl)-4-((3,4-dimethyl-1H-pyrazol-5-yl)amino)quinolin-7-yl)oxy)propan-2-ol

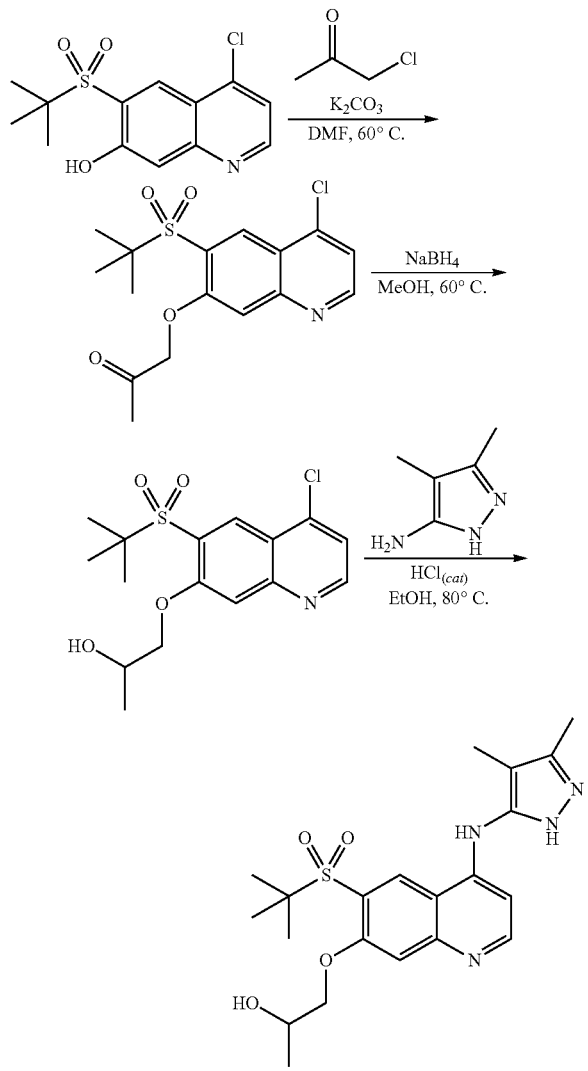

Step 1: 1-((6-(tert-butylsulfonyl)-4-chloroquinolin-7-yl)oxy)propan-2-one: To a solution of 6-(tert-butylsulfonyl)-4-chloroquinolin-7-ol (500 mg, 1.668 mmol) in DMF (8162 µl) was added $K_2CO_3$ (692 mg, 5.00 mmol) followed by 1-chloropropan-2-one (178 µl, 2.502 mmol). This was heated to 60° C. for 30 min. The crude sample was purified via Biotage normal phase chromatography (25 g SNAP column, 0%-65%, 65%. hex/EtOAc). The pure product containing-fractions were combined and concentrated leading to the product as an off-white solid: 1-((6-(tert-butylsulfonyl)-4-chloroquinolin-7-yl)oxy)propan-2-one (192 mg, 0.540 mmol, 32.3% yield). $^1$H NMR (400 MHz, DMSO-$d_6$) δ ppm 1.34 (s, 9H) 2.27 (s, 3H) 5.21 (s, 2H) 7.64 (s, 1H) 7.76 (d, J=4.80 Hz, 1H) 8.67 (s, 1H) 8.93 (d, J=4.80 Hz, 1H). MS: m/z: 356.1 [M+H]$^+$.

Step 2: 1-((6-(tert-butylsulfonyl)-4-chloroquinolin-7-yl)oxy)propan-2-ol: To a suspension of 1-((6-(tert-butylsulfonyl)-4-chloroquinolin-7-yl)oxy)propan-2-one (100 mg, 0.281 mmol) in MeOH (2810 µl) was added $NaBH_4$ (13.29 mg, 0.351 mmol) at rt. This was stirred at rt for 20 min. Removed solvent in vacuo. Redissolved in DCM and quenched with sat aq $NH_4Cl$. Separated and extracted twice more with DCM. Washed combined organics with brine, then dried on $MgSO_4$, filtered and concentrated providing 1-((6-(tert-butylsulfonyl)-4-chloroquinolin-7-yl)oxy)propan-2-ol (98.8 mg, 0.276 mmol, 98% yield) as an off-white foam. $^1$H NMR (400 MHz, DMSO-$d_6$) δ ppm 1.25 (d, J=6.06 Hz, 3H) 1.33 (s, 9H) 4.00-4.20 (m, 3H) 4.81 (d, J=4.29 Hz, 1H) 7.74 (s, 1H) 7.76 (d, J=4.80 Hz, 1H) 8.65 (s, 1H) 8.94 (d, J=4.80 Hz, 1H). MS: m/z: 358.1 [M+H]$^+$.

Step 3: 1-((6-(tert-butylsulfonyl)-4-((3,4-dimethyl-1H-pyrazol-5-yl)amino)quinolin-7-yl)oxy)propan-2-ol: To 1-((6-(tert-butylsulfonyl)-4-chloroquinolin-7-yl)oxy)propan-2-ol (98 mg, 0.274 mmol) and 3,4-dimethyl-1H-pyrazol-5-amine (39.6 mg, 0.356 mmol) was added EtOH (685 µl) followed by 1 drop of 2N aq HCl (9.99 mg, 0.274 mmol). The microwave vial was sealed and heated to 80° C. behind a blast shield overnight. Concentrated reaction. The crude sample was filtered and purified on a Gilson reverse phase HPLC system using a Sunfire C18 OBD 30×100 mm column with a gradient of 10-45% acetonitrile (0.1% TFA)/water (0.1% TFA) and a flow rate of 30 mL/min for 10 min. The pure product containing-fractions were combined and concentrated. Reconstituted resulting yellow residue in MeOH. Passed through a Biotage Si-Carbonate cartridge, rinsing with MeOH. Concentrated resulting in a yellowish solid. Triturated with $iPr_2O$ and filtered to provide the free base of the product as a pale yellow powder: 1-((6-(tert-butylsulfonyl)-4-((3,4-dimethyl-1H-pyrazol-5-yl)amino)quinolin-7-yl)oxy)propan-2-ol (51.3 mg, 0.116 mmol, 42.4% yield). $^1$H NMR (400 MHz, DMSO-$d_6$) δ ppm 1.24 (d, J=5.81 Hz, 3H) 1.32 (s, 9H) 1.76 (s, 3H) 2.18 (s, 4H) 3.91-4.13 (m, 3H) 4.72 (br. s., 1H) 6.37 (d, J=4.29 Hz, 1H) 7.37 (s, 1H) 8.38 (d, J=4.80 Hz, 1H) 8.92 (s, 1H) 9.33 (br. s., 1H). MS: m/z: 433.3 [M+H]$^+$.

Example 2

(R)-1-((6-(tert-Butylsulfonyl)-4-((3,4-dimethyl-1H-pyrazol-5-yl)amino)quinolin-7-yl)oxy)propan-2-ol, hydrochloride and (S)-1-((6-(tert-butylsulfonyl)-4-((3,4-dimethyl-1H-pyrazol-5-yl)amino)quinolin-7-yl)oxy)propan-2-ol, hydrochloride

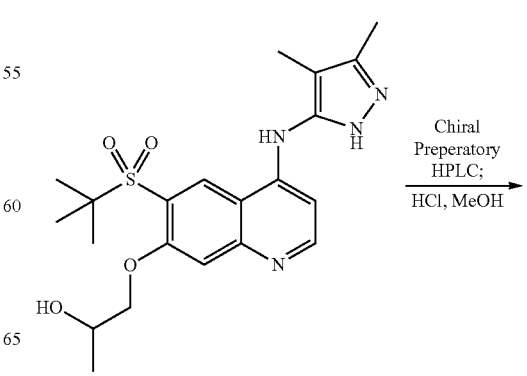

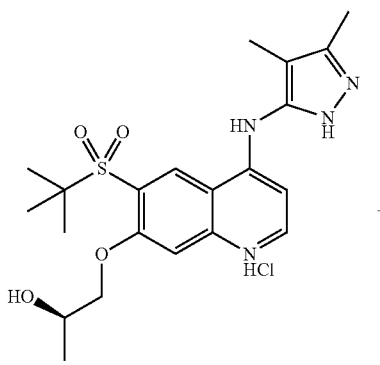

A racemic mixture of 1-((6-(tert-butylsulfonyl)-4-((3,4-dimethyl-1H-pyrazol-5-yl)amino)quinolin-7-yl)oxy)propan-2-ol was separated into its pure enantiomers by Chiral preparatory HPLC (Chiralpak AD-H 30×250 mm, available from Chiral Technologies, Inc., West Chester, Pa., USA. Eluent: 70:15:15-Heptane: EtOH:CH$_3$OH, 45 ml/min). (S)-1-((6-(tert-butylsulfonyl)-4-((3,4-dimethyl-1H-pyrazol-5-yl)amino)quinolin-7-yl)oxy)propan-2-ol eluted first (99.5% ee). (R)-1-((6-(tert-butylsulfonyl)-4-((3,4-dimethyl-1H-pyrazol-5-yl)amino)quinolin-7-yl)oxy)propan-2-ol eluted second (99.5% ee). The separated enantiomers were then individually dissolved into MeOH (needed to warm to 45° C. to dissolve), cooled to rt and then 1.5 eq. of 1.25 M HCl in MeOH was added and the solution was stirred for 10 minutes. Concentrated individual solutions and placed under vacuum yield a yellow solid. Triturated individual solids with ACN (20 mL) using sonication for 10 minutes. Filtered and dried the solids to yield the HCl salts of each of the enantiomers as light yellow/tan solids. Analytical data for (R)-1-((6-(tert-butylsulfonyl)-4-((3,4-dimethyl-1H-pyrazol-5-yl)amino)quinolin-7-yl)oxy)propan-2-ol, hydrochloride: $^1$H NMR (400 MHz, DMSO-d$_6$) δ ppm 14.47 (br. s., 1H), 12.73 (br. s., 1H), 11.24 (s, 1H), 9.24 (br. s., 1H), 8.50 (d, J=7.07 Hz, 1H), 7.67 (s, 1H), 6.64 (d, J=6.82 Hz, 1H), 3.97-4.18 (m, 3H), 2.24 (s, 3H), 1.84 (s, 3H), 1.35 (s, 9H), 1.28 (d, J=5.81 Hz, 3H), MS (m/z) 433. [α]$_D$=+0.4 deg (c=1.3, CH$_3$OH). m.p. 275-276° C. Analytical data for (S)-1-((6-(tert-butylsulfonyl)-4-((3,4-dimethyl-1H-pyrazol-5-yl)amino)quinolin-7-yl)oxy)propan-2-ol, hydrochloride: $^1$H NMR (400 MHz, DMSO-d$_6$) δ ppm 14.47 (br. s., 1H), 12.73 (br. s., 1H), 11.24 (s, 1H), 9.24 (br. s., 1H), 8.50 (d, J=7.07 Hz, 1H), 7.67 (s, 1H), 6.64 (d, J=6.82 Hz, 1H), 3.97-4.18 (m, 3H), 2.24 (s, 3H), 1.84 (s, 3H), 1.35 (s, 9H), 1.28 (d, J=5.81 Hz, 3H), MS (m/z) 433. [α]$_D$=−0.3 deg (c=1.3, CH$_3$OH). m.p. 266-267° C.

Example 3

(R)-1-((6-(tert-butylsulfonyl)-4-((3,4-dimethyl-1H-pyrazol-5-yl)amino)quinolin-7-yl)oxy)propan-2-ol, hydrochloride

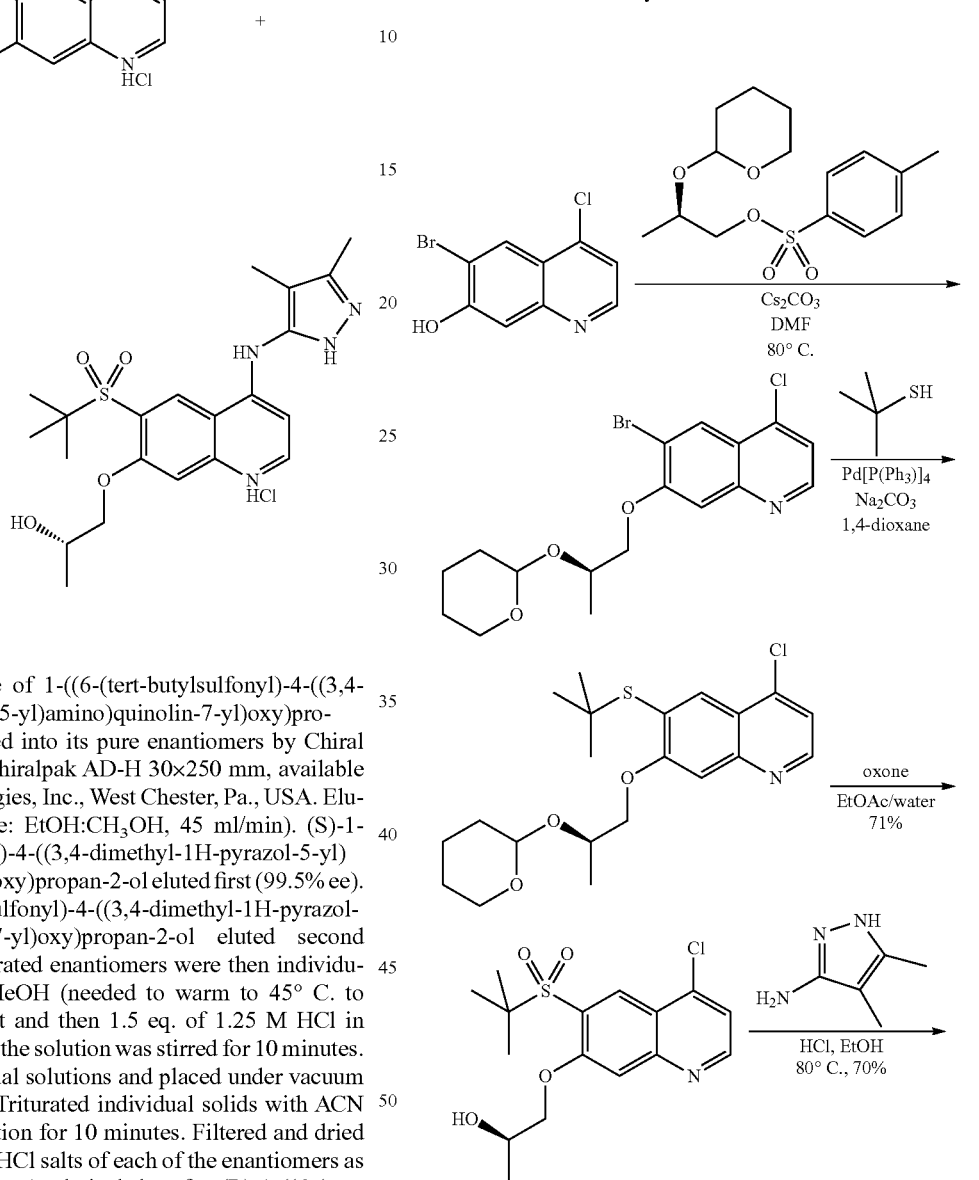

Step 1. 6-bromo-4-chloro-7-((2R)-2-((tetrahydro-2H-pyran-2-yl)oxy)propoxy)quinoline: A mixture of crude 6-bromo-4-chloroquinolin-7-ol (67.5 g, 206 mmol), (2R)-2-((tetrahydro-2H-pyran-2-yl)oxy)propyl 4-methylbenzenesulfonate (Jones, B. et. al. *J. Het. Chem.* 1982, 19(3), 551) (61.6 g, 196 mmol) and cesium carbonate (202 g, 619 mmol) in DMF (150 mL) was heated at 80° C. for 12 h, then stirred at 25° C. for 2 d. The reaction was added to a mixture of water (1200 mL) and Et$_2$O (500 mL). The organic layer was separated and washed with saturated aqueous NaHCO$_3$, brine, dried over MgSO$_4$, and concentrated in vacuo to give 6-bromo-4-chloro-7-((2R)-2-((tetrahydro-2H-pyran-2-yl)oxy)propoxy)quinoline as an oil (57.8 g, 69.9% yield). $^1$H NMR (400 MHz, DMSO-d$_6$) δ ppm 8.75-8.85 (m, 1H), 8.34-8.42 (m, 1H), 7.65 (d, J=4.8 Hz, 1H), 7.63 (d, J=4.0 Hz, 1H), 4.95-5.05 (m, 1H), 4.85 (t, J=3.0 Hz, 1H), 4.23-4.37 (m, 2H), 4.12-4.23 (m, 2H), 3.88-4.01 (m, 1H), 3.78-3.88 (m, 1H), 3.40-3.54 (m, 1H), 1.54-1.80 (m, 3H), 1.28 (m, 3H). MS (m/z) 402.0.

Step 2. 6-(tert-butylthio)-4-chloro-7-((2R)-2-((tetrahydro-2H-pyran-2-yl)oxy)propoxy)quinoline: A mixture of 6-bromo-4-chloro-7-((2R)-2-((tetrahydro-2H-pyran-2-yl)oxy)propoxy)quinoline (37.8 g, 94 mmol) in dioxane (397 ml) was purged with N$_2$ gas for 5 minutes with stirring. Tetrakis(triphenylphosphine)palladium (16.35 g, 14.15 mmol) and Na$_2$CO$_3$ (25.00 g, 236 mmol) were added, followed by 2-methylpropane-2-thiol (11.17 ml, 99 mmol). The reaction was purged (N$_2$) and evacuated 5 times, then stirred at 70° C. After 18 h, additional tetrakis(triphenylphosphine)palladium (1.6 g, 1.4 mmol) and 2-methylpropane-2-thiol (1.2 mL, 10.6 mmol) were added and the reaction mixture was heated to 70° C. again for 2 h. The reaction was cooled to RT and the mixture was filtered. The filtrate was concentrated in vacuo to a thick oil, which was dissolved into a mixture of hexanes (80 mL) and DCM (30 mL). The solution was purified over a pad of silica gel, eluting with 2 L of hexanes, followed by 4.5 L of 20% EtOAc in hexanes, and finally 2 L 50% ethyl acetate in hexanes to elute 6-(tert-butylthio)-4-chloro-7-((2R)-2-((tetrahydro-2H-pyran-2-yl)oxy)propoxy)quinoline (26.2 g, 67.8% yield) as a thick reddish-brown oil after removal of solvent in vacuo. $^1$H NMR (400 MHz, DMSO-d$_6$) δ ppm 8.78 (d, J=4.8 Hz, 1H), 8.26 (s, 1H), 7.62 (d, J=4.8 Hz, 1H), 7.54 (d, J=5.8 Hz, 1H), 5.00-5.22 (m, 1H), 4.73-4.97 (m, 1H), 4.14-4.28 (m, 4H), 4.03 (d, J=7.3 Hz, 1H), 3.75-3.86 (m, 2H), 3.38-3.61 (m, 3H), 1.69-1.80 (m, 2H), 1.58-1.65 (m, 1H), 1.32-1.34 (m, 9H). MS (m/z) 410.0.

Step 3. (R)-1-((6-(tert-butylsulfonyl)-4-chloroquinolin-7-yl)oxy)propan-2-ol: A mixture of 6-(tert-butylthio)-4-chloro-7-((2R)-2-((tetrahydro-2H-pyran-2-yl)oxy)propoxy)quinoline (30 g, 73.2 mmol) and oxone (67.5 g, 110 mmol) in EtOAc (362 ml) and water (362 ml) was stirred for 18 h at 25° C. The organic layer was separated, washed with saturated NaHCO$_3$ (100 mL) and the combined aqueous layers were basified with solid NaHCO$_3$ and extracted EtOAc (2×400 mL). The combined organic layers were dried over anhydrous MgSO$_4$ and concentrated in vacuo to provide an oil. This oil was dissolved in CH$_2$Cl$_2$ (50 mL) and purified by column chromatography (30 to 70% Hexanes to 3:1 EtOH:EtOAc, Isco Rf, 330 g silica gel column) to provide (R)-1-((6-(tert-butylsulfonyl)-4-chloroquinolin-7-yl)oxy)propan-2-ol (14.0 g, 53.5% yield) as a light peach solid after removal of solvent in vacuo. $^1$H NMR (400 MHz, DMSO-d$_6$) δ ppm 8.94 (d, J=4.8 Hz, 1H), 8.65 (s, 1H), 7.76 (d, J=4.8 Hz, 1H), 7.74 (s, 1H), 4.81 (d, J=4.3 Hz, 1H), 3.89-4.29 (m, 3H), 1.33 (s, 9H), 1.26 (d, J=6.1 Hz, 3H). MS (m/z) 358.0. This material was combined with additional batches and subjected to Pd scavenging: A solution of (R)-1-((6-(tert-butylsulfonyl)-4-chloroquinolin-7-yl)oxy)propan-2-ol (60.1 g, 134 mmol) in EtOH/CH$_2$Cl$_2$ (258 mL/258 mL) was stirred with Biotage Si-Thiol (335.9 mmol, 258.4 g, 1.3 mmol/g) for 4 h at 25° C. The mixture was filtered through glass filter paper, using EtOAc to transfer and rinse. The solid residue was rinsed with 2 L each of EtOH, EtOAc, and CH$_2$Cl$_2$. The filtrate was filtered again through glass filter paper, then concentrated in vacuo to yield a white solid, (R)-1-((6-(tert-butylsulfonyl)-4-chloroquinolin-7-yl)oxy)propan-2-ol (60 g, 125% yield), that may be used without further purification.

Step 4. (R)-1-((6-(tert-butylsulfonyl)-4-((3,4-dimethyl-1H-pyrazol-5-yl)amino)quinolin-7-yl)oxy)propan-2-ol, hydrochloride: A mixture of (R)-1-((6-(tert-butylsulfonyl)-4-chloroquinolin-7-yl)oxy)propan-2-ol (55 g, 154 mmol) and 3,4-dimethyl-1H-pyrazol-5-amine (22.21 g, 200 mmol) in EtOH (468 ml) and concentrated HCl (0.179 ml, 2.152 mmol) was stirred at 80° C. for 18 h. Additional 3,4-dimethyl-1H-pyrazol-5-amine (2.3 g, 20.7 mmol) in EtOH (100 mL) was added and the reaction mixture heated for 2 h. The reaction was cooled and concentrated in vacuo to a thick tan slurry. The slurry was heated in MeCN (240 mL) at reflux for 45 m with vigorous stirring. The reaction mixture was cooled to 25° C., sonicated for 1 minute, and the solid was filtered and washed with MeCN (50 mL). The filter cake was dried for 2 h, then dissolved in MeOH (1 L), heating to dissolve. The solution was concentrated in vacuo to give a thick mud (100 mL total volume). Acetonitrile (250 mL) was added to give a white precipitate. The mixture was heated at reflux for 1 h, then cooled 25° C. for 17 h. The white solid was filtered, washed with MeCN (50 mL) and dried under vacuum to give (R)-1-((6-(tert-butylsulfonyl)-4-((3,4-dimethyl-1H-pyrazol-5-yl)amino)quinolin-7-yl)oxy)propan-2-ol, hydrochloride (46.0 g, 63.8% yield) as a white solid, which was found to be a mono-HCl salt. The PXRD of a sample of this material is provided in FIG. 1. $^1$H NMR (400 MHz, DMSO-d$_6$) δ ppm 14.11-14.47 (m, 1H), 12.72 (s, 1H), 11.22 (br. s., 1H), 9.23 (br. s., 1H), 8.49 (d, J=6.9 Hz, 1H), 7.64 (s, 1H), 6.64 (d, J=6.9 Hz, 1H), 3.82-4.05 (m, 2H), 2.24 (s, 3H), 1.84 (s, 3H), 1.35 (s, 9H), 1.28 (d, J=5.8 Hz, 3H) MS (m/z) 477.0.

Example 4

1-((6-(tert-Butylsulfonyl)-4-((3,4-dimethyl-1H-pyrazol-5-yl)amino)quinolin-7-yl)oxy)-2-methylpropan-2-ol

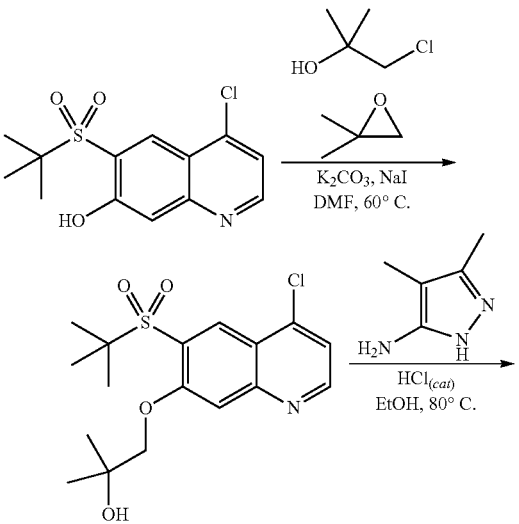

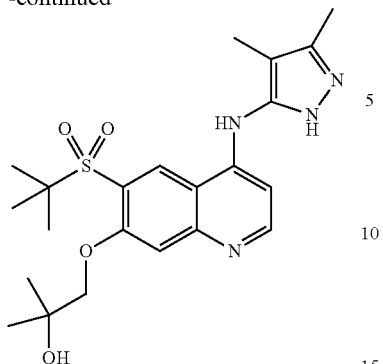

Step 1: 1-((6-(tert-butylsulfonyl)-4-chloroquinolin-7-yl)oxy)-2-methylpropan-2-ol: To a solution of 6-(tert-butylsulfonyl)-4-chloroquinolin-7-ol (250 mg, 0.834 mmol) in DMF (2756 μl) was added K$_2$CO$_3$ (576 mg, 4.17 mmol) followed by 1-chloro-2-methylpropan-2-ol (209 μl, 2.502 mmol). After 10 min, LCMS showed no product. Heated reaction to 60° C. No reaction after 3 hr at this temperature. Added sodium iodide (375 mg, 2.50 mmol) and 2,2-dimethyloxirane (371 μl, 4.17 mmol) and stirred for 2 days at to 60° C. The crude sample was purified via Biotage normal phase chromatography (25 g SNAP column, 0% -80%, 80%. hex/EtOAc). The pure product containing-fractions were combined and concentrated leading to the product as an off-white solid: 1-((6-(tert-butylsulfonyl)-4-chloroquinolin-7-yl)oxy)-2-methylpropan-2-ol (46 mg, 0.124 mmol, 14.83% yield). $^1$H NMR (400 MHz, DMSO-d$_6$) δ ppm 1.29 (s, 6H) 1.33 (s, 9H) 4.03 (s, 2H) 4.56 (s, 1H) 7.72 (s, 1H) 7.76 (d, J=4.80 Hz, 1H) 8.64 (s, 1H) 8.94 (d, J=4.80 Hz, 1H). MS (m/z) 372.2 (M+H$^+$).

Step 2: 1-((6-(tert-butylsulfonyl)-4-((3,4-dimethyl-1H-pyrazol-5-yl)amino)quinolin-7-yl)oxy)-2-methylpropan-2-ol: To 1-((6-(tert-butylsulfonyl)-4-chloroquinolin-7-yl)oxy)-2-methylpropan-2-ol (45 mg, 0.121 mmol) and 3,4-dimethyl-1H-pyrazol-5-amine (17.48 mg, 0.157 mmol) in a microwave vial was added EtOH (303 μl) followed by 1 drop of 1N aq HCl (4.41 mg, 0.121 mmol). The microwave vial was sealed and heated to 80° C. behind a blast shield overnight. LCMS showed full conversion to product. Concentrated reaction. The crude material was filtered and purified on a Gilson reverse phase HPLC system using a Sunfire C18 OBD 30×100 mm column with a gradient of 25-65% acetonitrile (0.1% TFA)/water (0.1% TFA) and a flow rate of 30 mL/min for 15 min. The pure product containing-fractions were combined and concentrated. The resulting yellow residue was reconstituted in MeOH and the resulting mixture was passed through a Biotage Si-Carbonate cartridge, which was rinsed with MeOH, then concentrated, resulting in a yellow solid. Triturated with iPr$_2$O and filtered to provide the free base of the product as an off-white powder: 1-((6-(tert-butylsulfonyl)-4-((3,4-dimethyl-1H-pyrazol-5-yl)amino)quinolin-7-yl)oxy)-2-methylpropan-2-ol (13.5 mg, 0.030 mmol, 24.98% yield). $^1$H NMR (400 MHz, DMSO-d$_6$) δ ppm 1.29 (s, 6H) 1.34 (s, 9H) 1.77 (s, 3H) 2.19 (s, 3H) 3.94 (s, 2H) 4.49 (s, 1H) 6.38 (br. s., 1H) 7.36 (s, 1H) 8.39 (d, J=5.31 Hz, 1H) 8.94 (s, 1H) 9.34 (s, 1H) 12.26 (br. s., 1H). MS (m/z) 447.3 (M+H$^+$).

Example 5

6-(tert-Butylsulfonyl)-7-(2,2-difluoroethoxy)-N-(3,4-dimethyl-1H-pyrazol-5-yl)quinolin-4-amine

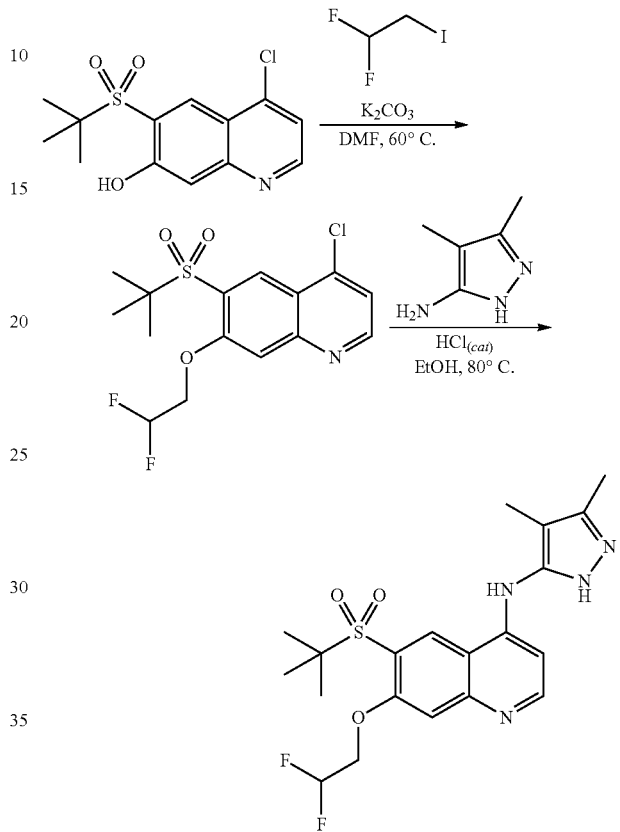

Step 1: 6-(tert-butylsulfonyl)-4-chloro-7-(2,2-difluoroethoxy)quinoline: To a solution of 6-(tert-butylsulfonyl)-4-chloroquinolin-7-ol (100 mg, 0.334 mmol) was added K$_2$CO$_3$ (138 mg, 1.001 mmol) followed by 1,1-difluoro-2-iodoethane (44.1 μl, 0.500 mmol). This was heated to 60° C. overnight. LCMS showed incomplete conversion. Additional 1,1-difluoro-2-iodoethane (44.1 μl, 0.500 mmol) was added and the reaction was stirred at 60° C. for 5 hr. Reaction was still not complete by LCMS, so another aliquot of 1,1-difluoro-2-iodoethane (44.1 μl, 0.500 mmol) was added and the reaction was stirred at 60° C. overnight again. LCMS showed complete and clean conversion to the desired product. The crude sample was purified via Biotage normal phase chromatography (25 g SNAP column, 0% -50%, 50% hex/EtOAc). The pure product containing-fractions were combined and concentrated leading to the product as an off-white solid: 6-(tert-butylsulfonyl)-4-chloro-7-(2,2-difluoroethoxy)quinoline (88.8 mg, 0.244 mmol, 73.2% yield). $^1$H NMR (400 MHz, DMSO-d$_6$) δ ppm 1.32 (s, 9H) 4.66 (td, J=14.53, 3.54 Hz, 2H) 6.28-6.63 (m, 1H) 7.80 (d, J=4.80 Hz, 1H) 7.85 (s, 1H) 8.67 (s, 1H) 8.97 (d, J=4.80 Hz, 1H). MS: m/z: 364.1 [M+H]$^+$.

Step 2: 6-(tert-butylsulfonyl)-7-(2,2-difluoroethoxy)-N-(3,4-dimethyl-1H-pyrazol-5-yl)quinolin-4-amine: To 6-(tert-butylsulfonyl)-4-chloro-7-(2,2-difluoroethoxy)quinoline (85 mg, 0.234 mmol) and 3,4-dimethyl-1H-pyrazol-5-amine (33.8 mg, 0.304 mmol) in a microwave vial was added EtOH (779 μl) followed by 1 drop of 1N aq HCl (8.52 mg, 0.234 mmol). The vial was sealed and heated to 80° C. behind a blast shield overnight. LCMS showed full conversion to product.

Concentrated reaction and triturated resulting residue with ~2 mL of MeCN using ~1 min of sonication. Filtered resulting solid, rinsing with MeCN, and dried under vacuum resulting in the product 6-(tert-butylsulfonyl)-7-(2,2-difluoroethoxy)-N-(3,4-dimethyl-1H-pyrazol-5-yl)quinolin-4-amine, hydrochloride (93.5 mg, 0.197 mmol, 84% yield) as an off-white solid. $^1$H NMR (400 MHz, DMSO-$d_6$) δ ppm 12.70 (s, 1H), 11.25 (br. s., 1H), 9.26 (br. s., 1H), 8.51 (d, J=7.07 Hz, 1H), 7.57 (s, 1H), 6.67 (d, J=7.33 Hz, 1H), 6.47 (tt, J=3.28, 53.81 Hz, 1H), 4.63 (td, J=3.16, 14.46 Hz, 2H), 2.24 (s, 3H), 1.84 (s, 3H), 1.34 (s, 9H). MS: m/z: 439.3 [M+H]$^+$.

Example 6

6-(tert-Butylsulfonyl)-N-(3,4-dimethyl-1H-pyrazol-5-yl)-7-(3-methoxypropoxy)quinolin-4-amine

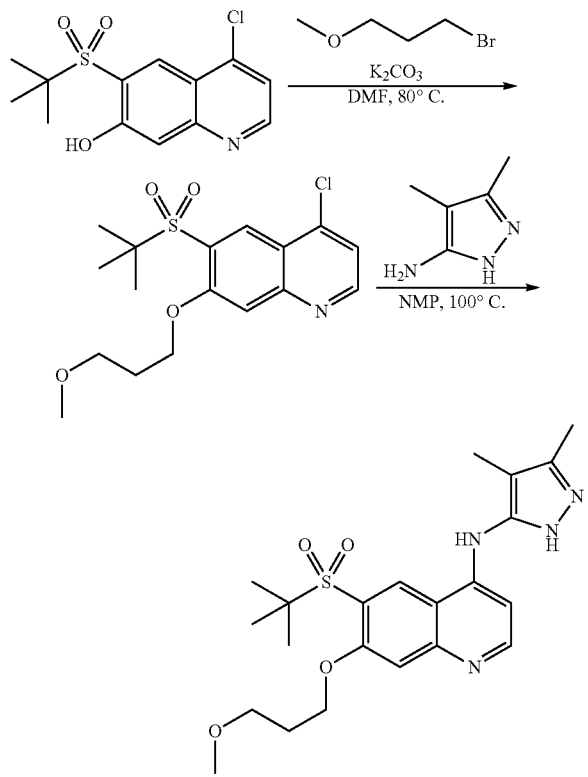

Step 1: 6-(tert-butylsulfonyl)-4-chloro-7-(3-methoxypropoxy)quinoline: 6-(tert-Butylsulfonyl)-4-chloroquinolin-7-ol (60 mg, 0.196 mmol), $K_2CO_3$ (55 mg, 0.392 mmol) and 1-bromo-3-methoxypropane (0.088 ml, 0.785 mmol) in DMF (1 ml) were heated to 70° C. The reaction mixture was partitioned between EtOAc and brine. The aqueous layer was extracted with EtOAc twice and the combined EtOAc layers were dried over $Na_2SO_4$, filtered, and concentrated. The residue was purified via Biotage (SNAP Cartridge KP Sil 10 g, 30-75% EtOAc/Hexane) to yield 6-(tert-butylsulfonyl)-4-chloro-7-(3-methoxypropoxy)quinoline (0.071 g, 0.185 mmol, 94% yield). $^1$H NMR (400 MHz, DMSO-$d_6$) δ ppm 1.33 (s, 9H) 1.99-2.08 (m, 2H) 3.27 (s, 3H) 3.58 (t, J=6.19 Hz, 2H) 4.32 (t, J=6.19 Hz, 2H) 7.73 (s, 1H) 7.76 (d, J=4.80 Hz, 1H) 8.65 (s, 1H) 8.94 (d, J=4.55 Hz, 1H), MS: m/z: 372.1 [M+H]$^+$.

Step 2: 6-(tert-butylsulfonyl)-N-(3,4-dimethyl-1H-pyrazol-5-yl)-7-(3-methoxypropoxy)quinolin-4-amine: To a solution of 6-(tert-butylsulfonyl)-4-chloro-7-(3-methoxypropoxy)quinoline (0.07 g, 0.184 mmol) in NMP (1 mL) was added 4,5-dimethyl-1H-pyrazol-3-amine (0.025 g, 0.221 mmol). The reaction was heated at 100° C. The reaction mixture cooled and then purified via reverse phase HPLC (Waters Sunfire C18, 30×100 mm, 10-50% acetonitrile/water 0.1% TFA, 35 ml/min, 10 mins) to yield trifluoroacetic acid salt. The salt was basified with saturated $Na_2CO_3$, then extracted with dichloromethane. The DCM layer was dried over $Na_2SO_4$, filtered, concentrated and vacuum dried to yield 6-(tert-butylsulfonyl)-N-(3,4-dimethyl-1H-pyrazol-5-yl)-7-(3-methoxypropoxy)quinolin-4-amine (0.050 g, 0.104 mmol, 56.4% yield). $^1$H NMR (400 MHz, DMSO-$d_6$) δ ppm 1.33 (s, 9H) 1.78 (s, 3H) 1.98-2.06 (m, 2H) 2.20 (s, 3H) 3.27 (s, 3H) 3.59 (t, J=6.32 Hz, 2H) 4.22 (t, J=6.06 Hz, 2H) 6.38 (br. s., 1H) 7.37 (s, 1H) 8.39 (d, J=5.56 Hz, 1H) 8.94 (s, 1H) 9.33 (br. s., 1H) 12.27 (br. s., 1H), MS: m/z: 447.2 [M+H]$^+$.

The following example was synthesized in the same manner as the above example, using $CF_3CH_2I$ as the alkylating agent:

| Ex. | Structure | Name | MS (M + H)$^+$ | NMR |
|---|---|---|---|---|
| 7 | 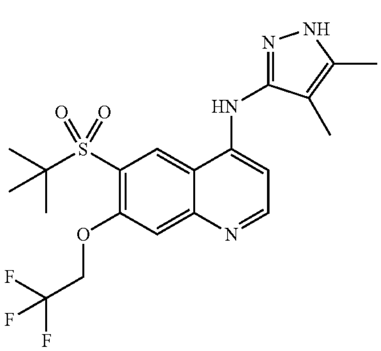 [SMILES: Cc1[nH]nc(Nc2ccnc3cc(OCC(F)(F)F)c(S(=O)(=O)C(C)(C)C)cc23)c1C] | 6-(tert-butylsulfonyl)-N-(4,5-dimethyl-1H-pyrazol-3-yl)-7-(2,2,2-trifluoroethoxy)quinolin-4-amine | 457 | $^1$H NMR (400 MHz, CHLOROFORM-d) δ ppm 9.03 (s, 1 H), 8.49 (d, J = 5.56 Hz, 1 H), 7.58 (br. s., 1 H), 6.39 (d, J = 5.56 Hz, 1 H), 4.59 (q, J = 8.08 Hz, 2 H), 2.34 (s, 3 H), 1.80 (s, 3 H), 1.42 (s, 9 H) |

Example 8

6-(tert-Butylsulfonyl)-N-(3,4-dimethyl-1H-pyrazol-5-yl)-7-(2-methoxyethoxy)quinolin-4-amine, hydrochloride

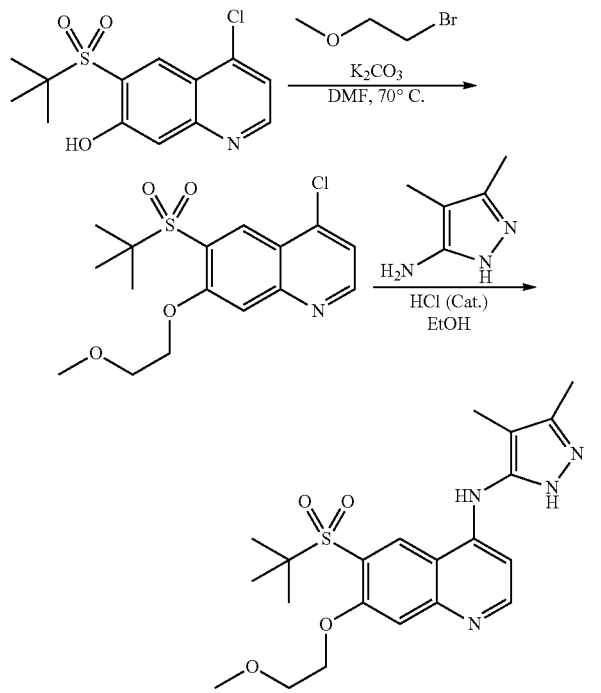

Step 1: 6-(tert-butylsulfonyl)-4-chloro-7-(2-methoxyethoxy)quinoline: 6-(tert-Butylsulfonyl)-4-chloroquinolin-7-ol (0.81 g, 2.70 mmol), $K_2CO_3$ (1.143 g, 8.11 mmol), and 1-bromo-2-methoxyethane (0.508 ml, 5.40 mmol) in DMF (8.50 ml) were heated at 70° C. The reaction mixture cooled and partitioned between EtOAc and brine. The aqueous layer was extracted with EtOAc twice and the combined EtOAc layers were dried over $Na_2SO_4$, filtered, and concentrated. The residue was purified via Biotage (SNAP Cartridge KP Sil 25 g, 10-50% EtOAc/Hexane) to yield 6-(tert-butylsulfonyl)-4-chloro-7-(2-methoxyethoxy)quinoline (0.461 g, 1.262 mmol, 46.7% yield). $^1$H NMR (400 MHz, DMSO-$d_6$) δ ppm 8.93 (d, J=4.55 Hz, 1H), 8.66 (s, 1H), 7.73-7.79 (m, 2H), 4.40 (dd, J=3.54, 5.31 Hz, 2H), 3.76 (dd, J=3.66, 5.18 Hz, 2H), 3.34 (s, 3H), 1.33 (s, 9H), MS: m/z: 358.1 [M+H]$^+$.

Step 2: 6-(tert-butylsulfonyl)-N-(3,4-dimethyl-1H-pyrazol-5-yl)-7-(2-methoxyethoxy)quinolin-4-amine, hydrochloride: 6-(tert-Butylsulfonyl)-4-chloro-7-(2-methoxyethoxy)quinoline (0.461 g, 1.288 mmol), 4,5-dimethyl-1H-pyrazol-3-amine (0.175 g, 1.546 mmol), and 2 drops of aq HCl (0.161 ml, 0.322 mmol) in EtOH (3.06 ml) were heated at 80° C. overnight. The reaction was cooled to rt and the precipitate was filtered, washed with MeCN, and vacuum-dried to yield 6-(tert-butylsulfonyl)-N-(3,4-dimethyl-1H-pyrazol-5-yl)-7-(2-methoxyethoxy)quinolin-4-amine, hydrochloride (0.290 g, 0.618 mmol, 48.0% yield). m.p. 181-184° C. $^1$H NMR (400 MHz, DMSO-$d_6$) δ ppm 12.71 (s, 1H), 11.20 (br. s., 1H), 9.22 (br. s., 1H), 8.48 (d, J=7.07 Hz, 1H), 7.63 (s, 1H), 6.64 (d, J=7.07 Hz, 1H), 4.36 (t, J=4.29 Hz, 2H), 3.78 (t, J=4.29 Hz, 2H), 3.35 (s, 3H), 2.24 (s, 3H), 1.84 (s, 3H), 1.35 (s, 9H). MS: m/z: 433.2 [M+H]$^+$.

Example 9

6-(tert-butylsulfonyl)-N-(4,5-dimethyl-1H-pyrazol-3-yl)-7-(2-methoxyethoxy)quinolin-4-amine, hydrochloride, monohydrate

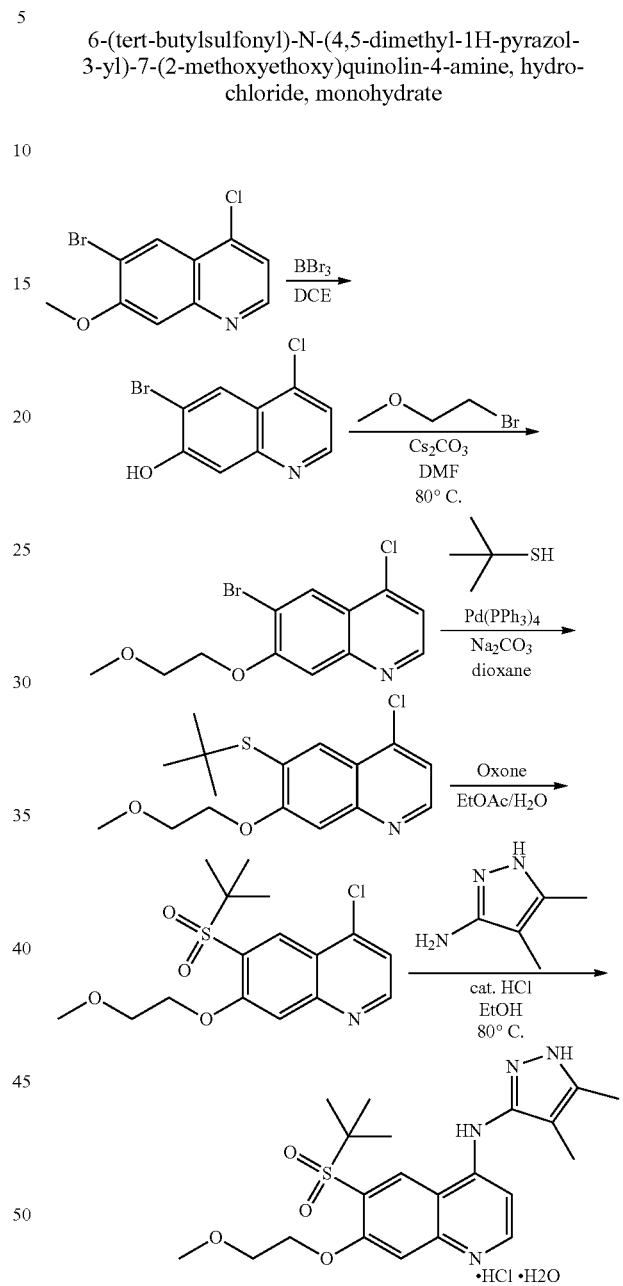

Step 1. 6-bromo-4-chloroquinolin-7-ol: A mixture of 6-bromo-4-chloro-7-methoxyquinoline (50.00 g, 183 mmol) and boron tribromide (37.3 ml, 394 mmol) in DCE (200 ml) was stirred under nitrogen at 90° C. for 2.5 h. The reaction mixture was cooled to RT and poured into saturated $NaHCO_3$ with vigorous stirring. The solid was filtered and washed with water and dried to yield ~83 g of a brown solid. This material was divided into 2 equal batches. Each batch was placed in a 1 L round bottom flask along with 500 mL of i-$Pr_2O$ and heated at 70° C. for 15 minutes. The mixture solidified; cooled to RT, diluted with more i-$Pr_2O$, and filtered, then dried to yield 6-bromo-4-chloroquinolin-7-ol (59.99 g, 126%) as a brown solid. This sample is likely contaminated with inorganic salts which would account for the extra weight. $^1$H NMR (400 MHz, DMSO-$d_6$) δ 8.97 (d, J=5.56 Hz, 1H), 8.48 (s, 1H), 7.85 (d, J=5.56 Hz, 1H), 7.60 (s, 1H). MS (m/z) 258/260.

Step 2. 6-bromo-4-chloro-7-(2-methoxyethoxy)quinoline: A mixture of 6-bromo-4-chloroquinolin-7-ol (42.82 g, 166 mmol), 1-bromo-2-methoxyethane (18.68 ml, 199 mmol) and cesium carbonate (162 g, 497 mmol) in DMF (395 ml) was stirred under nitrogen at 80° C. for 4 hours. The reaction mixture was cooled to RT and water (~500 mL) was added. Approximately ~1/16 of mixture was poured into water (500 mL) and the solid was filtered. This process was repeated until all of sample was consumed, filtering the solid each time in the same Buchner funnel. After filtering, the solid was washed with 1500 mL of water and dried under vacuum for several hours, then transferred into a crystallizing dish and placed in a drying oven under vacuum at 80° C. for 65 hours to yield 6-bromo-4-chloro-7-(2-methoxyethoxy)quinoline (27.38 g, 52.2%) as a brown solid. $^1$H NMR (400 MHz, DMSO-$d_6$) δ 8.81 (d, J=4.80 Hz, 1H), 8.38 (s, 1H), 7.66 (d, J=4.80 Hz, 1H), 7.63 (s, 1H), 4.37-4.41 (m, 2H), 3.77-3.82 (m, 2H), 3.38 (s, 3H). MS (m/z) 316/318.

Step 3. 6-(tert-butylthio)-4-chloro-7-(2-methoxyethoxy) quinoline: A mixture of 6-bromo-4-chloro-7-(2-methoxyethoxy)quinoline (27.18 g, 86 mmol) in 1,4-dioxane (300 ml) was stirred at RT while purging with nitrogen for 20 minutes. After the purging was complete, Na$_2$CO$_3$ (22.75 g, 215 mmol), tetrakis(triphenylphosphine)palladium (2.480 g, 2.146 mmol) and 2-methylpropane-2-thiol (10.16 ml, 90 mmol) were added and the reaction was heated at 70° C. for 3 h. Only minimal progress was observed; another batch of Pd(PPh$_3$)$_4$ (2.480 g, 2.146 mmol) and 2-methylpropane-2-thiol (10.16 ml, 90 mmol) was added and heating was continued for 2 h. This process was repeated twice at which time all of the starting bromide was consumed. The reaction mixture was cooled to RT and passed through a plug of silica gel (pre-wetted with EtOAc), using ethyl acetate to elute out product. The eluate was concentrated to yield a black oil. This material was reconcentrated onto Celite and divided into 2 batches for purification. Each batch was purified as follows: the crude samples were purified via Isco normal phase chromatography (330 g column, 0%-60%, EtOAc/Hexanes). The pure product containing-fractions were combined and concentrated leading to the product: 6-(tert-butylthio)-4-chloro-7-(2-methoxyethoxy)quinoline (25.53 g, 91%) as a brown solid. $^1$H NMR (400 MHz, DMSO-$d_6$) δ 8.76-8.80 (m, 1H), 8.26 (s, 1H), 7.60-7.66 (m, 1H), 7.55 (s, 1H), 4.25-4.39 (m, 2H), 3.68-3.83 (m, 2H), 3.37 (s, 3H), 1.32 (s, 9H). MS (m/z) 326.

Step 4. 6-(tert-butylsulfonyl)-4-chloro-7-(2-methoxyethoxy)quinoline: A mixture of 6-(tert-butylthio)-4-chloro-7-(2-methoxyethoxy)quinoline (25.51 g, 78 mmol) in EtOAc (300 mL) and water (300 mL) was stirred at RT. Next, Oxone® (55.3 g, 90 mmol) was added portionwise over 10 minutes followed by stirring overnight. The reaction was not complete; an additional 5.5 g of Oxone® (0.1 eq.) was added and the reaction mixture was stirred for 1 h. This process was repeated twice, after which, the reaction was complete. The resulting reaction mixture was poured into separatory funnel and the layers were separated. The aqueous layer was extracted three times with EtOAc. The combined organics were concentrated to yield orange oil that solidified upon standing. This material was dissolved into CH$_2$Cl$_2$, concentrated onto Celite, and divided into 2 batches for purification. Each batch was purified as follows: the crude sample was purified via Isco normal phase chromatography (330 g Gold column, 0%-100%, EtOAc/Hexanes). The pure product containing-fractions were combined and concentrated leading to the product: 6-(tert-butylsulfonyl)-4-chloro-7-(2-methoxyethoxy)quinoline (19.51 g, 69.6%) as a light orange solid. $^1$H NMR (400 MHz, DMSO-$d_6$) δ 8.93 (d, 1H), 8.66 (s, 1H), 7.62-7.82 (m, 2H), 4.31-4.46 (m, 2H), 3.68-3.81 (m, 2H), 3.34 (s, 3H), 1.32 (s, 9H). MS (m/z) 358. This material was combined with additional batches and subjected to Pd scavenging: 6-(tert-butylsulfonyl)-4-chloro-7-(2-methoxyethoxy)quinoline material (24.18 g, 67.57 mmol) was dissolved in 3:1 DCM:EtOH. To this solution was added Biotage Si-Thiol resin (270.28 mmol, 207.6 g, 4 eq) and the resulting suspension was stirred for 4 hours at room temperature. The suspension was filtered through a pad of Celite using CH$_2$Cl$_2$ to rinse. The filtrate was concentrated to yield 6-(tert-butylsulfonyl)-4-chloro-7-(2-methoxyethoxy)quinoline (26 g) as a viscous yellow oil, which may be used without further purification.

Step 5. 6-(tert-butylsulfonyl)-N-(4,5-dimethyl-1H-pyrazol-3-yl)-7-(2-methoxyethoxy)quinolin-4-amine, hydrochloride, monohydrate: A mixture of 6-(tert-butylsulfonyl)-4-chloro-7-(2-methoxyethoxy)quinoline (24 g, 67.1 mmol) and 4,5-dimethyl-1H-pyrazol-3-amine (9.69 g, 87 mmol) and 6N HCl (several drops via pipette) in EtOH (200 ml) was stirred under nitrogen at 80° C. overnight. The reaction mixture was cooled to RT. Most of the EtOH was removed in vacuo until thick slurry remained. MeCN (700 mL) was added and the suspension was heated at reflux for 45 minutes with vigorous stirring. The suspension was cooled to RT, then sonicated for 15 minutes. The solid was filtered, rinsing with MeCN. The material was dried under suction for 45 minutes then transferred to a round bottom flask and placed under vacuum for several hours (yielded 28.5 g). The solid was then placed in a vacuum oven at 50° C. overnight. The resulting solid was transferred to a crystallizing dish and manually ground into more of a free flowing powder followed by continued heating in a vacuum oven for 48 h. The sample was subjected to further grinding and was placed in a vacuum oven again at 50° C. overnight to yield 6-(tert-butylsulfonyl)-N-(4,5-dimethyl-1H-pyrazol-3-yl)-7-(2-methoxyethoxy) quinolin-4-amine, hydrochloride, monohydrate (26.9 g, 86%) as a pale yellow powder, which was found to be a mono-HCl salt and a mono-hydrate. The PXRD of a sample of this material is provided in FIG. 2. $^1$H NMR (400 MHz, DMSO-$d_6$) δ 14.05-14.15 (m, 1H), 12.69 (s, 1H), 11.21 (br. s., 1H), 9.24 (br. s., 1H), 8.49 (d, J=7.07 Hz, 1H), 7.55 (s, 1H), 6.65 (d, J=6.82 Hz, 1H), 4.32-4.43 (m, 2H), 3.73-3.83 (m, 2H), 3.35 (s, 3H), 2.24 (s, 3H), 1.84 (s, 3H), 1.35 (s, 9H). MS (m/z) 433.

Example 10

6-(tert-Butylsulfonyl)-N-(3,4-dimethyl-1H-pyrazol-5-yl)-7-fluoroquinolin-4-amine

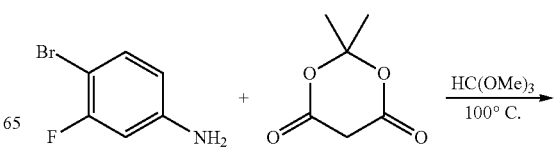

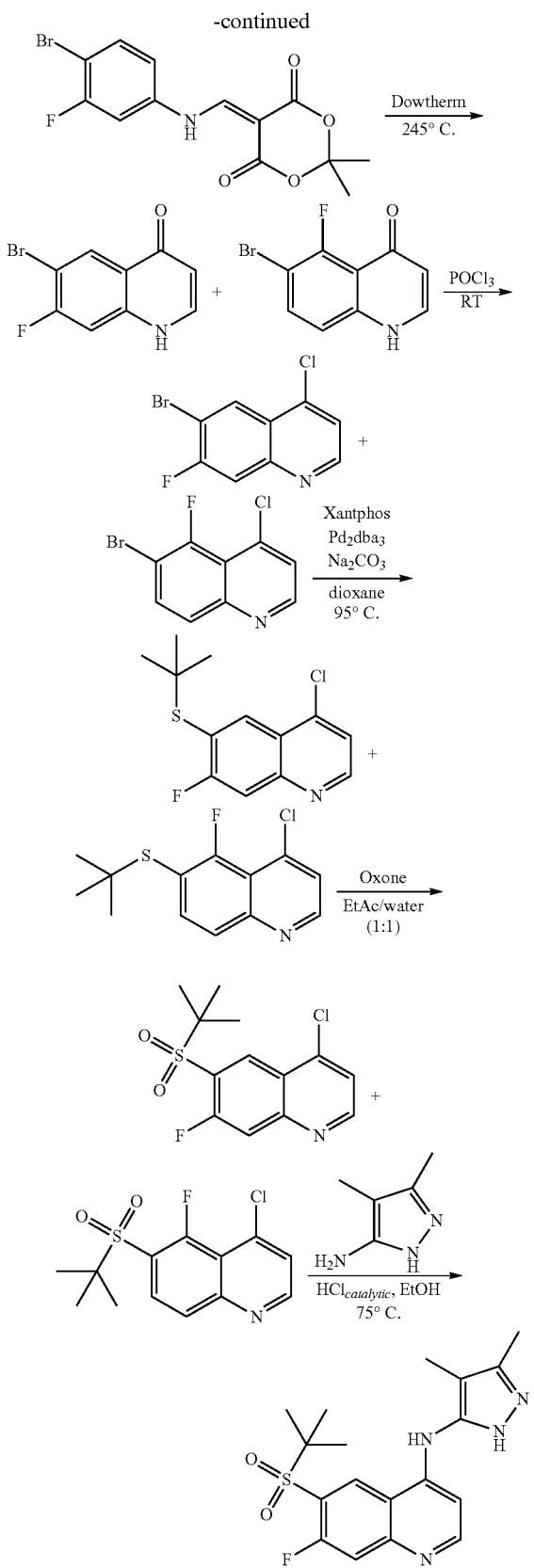

orthoformate (125 mL) was stirred at 100° C. for 1.5 h. This mixture was cooled to 80° C. and 4-bromo-3-fluoroaniline (40 g, 211 mmol) was added using ACN to aid in transfer. Heated to 100° C. for 3.5 h. The reaction mixture was cooled to RT and poured into Et₂O (750 mL) and stirred for a few minutes. Filtered resulting solid, washing with Et₂O and dried to yield 5-(((4-bromo-3-fluorophenyl)amino)methylene)-2,2-dimethyl-1,3-dioxane-4,6-dione (61.41 g, 178 mmol, 85% yield) as a light yellow powder. $^1$H NMR (DMSO-$d_6$) δ ppm 11.25 (d, J=14.4 Hz, 1H), 8.59 (d, J=14.4 Hz, 1H), 7.67-7.85 (m, 2H), 7.42 (dd, J=8.6, 2.0 Hz, 1H), 1.68 (s, 6H).

Step 2: 6-bromo-7-fluoroquinolin-4(1H)-one/6-bromo-5-fluoroquinolin-4(1H)-one. 5-(((4-Bromo-3-fluorophenyl) amino)methylene)-2,2-dimethyl-1,3-dioxane-4,6-dione (61.14 g, 177.6 mmol) was added portion-wise to Dowtherm (270 mL) at 245° C. After the addition, stirred at 245° C. for 20 minutes. Cool to RT. Added hexanes (~830 mL) and filtered the solid washing with additional hexanes and dried the solid to yield 6-bromo-7-fluoroquinolin-4(1H)-one/6-bromo-5-fluoroquinolin-4(1H)-one (38.02 g, 88.5%) as brown solid and as a mixture of regioisomers (46:54, by LCMS). MS: m/z: 242.0/244.0 [M+H]+. Used this mixture as is for the next step.

Step 3: 6-bromo-4-chloro-7-fluoroquinoline/6-bromo-4-chloro-5-fluoroquinoline. A mixture of 6-bromo-7-fluoroquinolin-4(1H)-one/6-bromo-5-fluoroquinolin-4(1H)-one (37.6 g, 155 mmol) and phosphorus oxychloride (101 ml, 1087 mmol) was stirred at RT overnight. The POCl₃ was removed via rotovap and the resulting material was dissolved into DCM. This mixture was quenched (very carefully) via pipette addition of sat. aq. Na₂CO₃. Once the mixture was neutralized, the layers were separated. The aqueous layer was further extracted with DCM. The combined organic layers were concentrated. The resulting material was taken into EtOAc and passed through a short plug of silica gel and concentrated to yield 6-bromo-4-chloro-7-fluoroquinoline/6-bromo-4-chloro-5-fluoroquinoline (40.42 g, 100%) of a brown solid that was a mixture of regioisomers (31:69, by LCMS). MS: m/z: 260.0/262.0 [M+H]+.

Step 4: 6-(tert-butylthio)-4-chloro-7-fluoroquinoline/6-(tert-butylthio)-4-chloro-5-fluoroquinoline. A mixture of 6-bromo-4-chloro-7-fluoroquinoline/6-bromo-4-chloro-5-fluoroquinoline (20.35 g, 78 mmol), 2-methylpropane-2-thiol (9.68 ml, 86 mmol), sodium Na₂CO₃ (24.84 g, 234 mmol), Pd₂dba₃ (7.15 g, 7.81 mmol), and Xantphos (4.52 g, 7.81 mmol) in 1,4-Dioxane (300 ml) was stirred under nitrogen at 95° C. overnight. Cooled to RT and concentrated. Dissolved resulting material into DCM/water, and separated the layers. Extracted aqueous layer with DCM. The combined organic layers were concentrated. The crude sample was purified via Isco normal phase chromatography (330 g column, 0% -15%, E/H) to yield 6-(tert-butylthio)-4-chloro-7-fluoroquinoline/6-(tert-butylthio)-4-chloro-5-fluoroquinoline (~20.5 g) as a yellow solid that still contained dba. MS: m/z: 270.0 [M+H]+. This sample was a mixture of regioisomers that was used as is for next step.

Step 5: 6-(tert-butylsulfonyl)-4-chloro-7-fluoroquinoline/6-(tert-butylsulfonyl)-4-chloro-5-fluoroquinoline. A mixture of 6-(tert-butylthio)-4-chloro-7-fluoroquinoline and 6-(tert-butylthio)-4-chloro-5-fluoroquinoline (21.24 g, 79 mmol) and oxone (48.4 g, 79 mmol) in EtOAc (200 ml) and water (200 ml) was stirred at RT overnight. LCMS showed sulfoxide as well as sulfone. Added an additional 15 g of Oxone and stirred for 3 hours; the sulfoxide was still present. Added 15 g more of Oxone and stirred for 3 hours more. Sulfoxide was still present. Added 5 g more of Oxone and stirred overnight.

Step 1: 5-(((4-bromo-3-fluorophenyl)amino)methylene)-2,2-dimethyl-1,3-dioxane-4,6-dione. A mixture of 2,2-dimethyl-1,3-dioxane-4,6-dione (36.4 g, 253 mmol) in trimethyl Note each time more Oxone was added the amounts of EtOAc and water needed to be increased as well. The final amounts of solvent were ~500 mL EtOAc and ~500 mL water. The layers were separated and the aqueous layer was extracted once with ethyl acetate. The combined organics were filtered and concentrated. Split material into 2 batches for purification. Each batch was purified as follows: The crude sample was purified via Isco normal phase chromatography (330 g Gold column, 0%-20%, E/H). This purification yielded separation of the regioisomers. The two batches of purified products were recombined. Peak 1 was the 6-(tert-butylthio)-4-chloro-7-fluoroquinoline product (9.86 g) as a creamy white solid. $^1$H NMR (ACETONITRILE-d$_3$) δ ppm 8.96 (d, 1H), 8.77 (d, J=7.3 Hz, 1H), 7.99 (d, J=11.4 Hz, 1H), 7.74 (d, J=4.8 Hz, 1H), 1.41 (d, J=1.0 Hz, 9H). MS: m/z: 302.0 [M+H]+. Peak 2 was the 6-(tert-butylsulfonyl)-4-chloro-5-fluoroquinoline product (1.71 g) as a white powder. $^1$H NMR (ACETONITRILE-d$_3$) δ ppm 8.94 (d, 1H), 8.04-8.15 (m, 2H), 7.75 (d, J=4.8 Hz, 1H), 1.41 (d, J=1.3 Hz, 9H). MS: m/z: 302.0 [M+H]+.

Step 6: 6-(tert-butylsulfonyl)-N-(3,4-dimethyl-1H-pyrazol-5-yl)-7-fluoroquinolin-4-amine. A mixture of 6-(tert-butylsulfonyl)-4-chloro-7-fluoroquinoline (0.200 g, 0.663 mmol) and 3,4-dimethyl-1H-pyrazol-5-amine (0.110 g, 0.994 mmol) in EtOH (3 mL) containing 3 drops (via syringe) of 1N aq. HCl was stirred at 75° C. overnight. Cooled and pass through a Biotage Si-Carbonate cartridge, rinsing with MeOH. The MeOH washings were concentrated and the crude sample was purified via Isco normal phase chromatography (12 g Gold column, 0% -10%, MeOH/DCM). All fractions containing product were combined and concentrated to yield ~300 mg of a yellow foamy solid (>100%). Dissolved into ACN and sonicated; a white precipitate formed. Placed in Genevac (to centrifuge the material) and removed liquid. Triturated the resulting material with Et$_2$O and filtered, washing the solid with additional Et$_2$O and hexanes. Dried the solid to yield 6-(tert-butylsulfonyl)-N-(3,4-dimethyl-1H-pyrazol-5-yl)-7-fluoroquinolin-4-amine as a white powder. $^1$H NMR (DMSO-d$_6$) δ ppm 12.33 (s, 1H), 9.56 (s, 1H), 9.05 (d, J=7.3 Hz, 1H), 8.49 (d, J=5.6 Hz, 1H), 7.74 (d, J=12.1 Hz, 1H), 6.47-6.58 (m, 1H), 2.21 (s, 3H), 1.79 (s, 3H), 1.36 (s, 9H). MS: m/z: 377.0 [M+H]+.

Pharmaceutical Compositions

Example A

Tablets are prepared using conventional methods and are formulated as follows:

| Ingredient | Amount per tablet |
| --- | --- |
| Compound of Example 1 | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
| --- | --- |
| Compound of Example 3 | 15 mg |
| Dried starch | 178 mg |
| Magnesium stearate | 2 mg |
| Total | 195 mg |

Biological Assay:

A fluorescent polarization based binding assay was developed to quantitate interaction of novel test compounds at the ATP binding pocket of RIPK2, by competition with a fluorescently labeled ATP competitive ligand. Full length FLAG His tagged RIPK2 was purified from a Baculovirus expression system and was used at a final assay concentration of twice the KDapparent. A fluorescent labeled ligand (5-({[2-({[3-({4-[(5-hydroxy-2-methylphenyl)amino]-2-pyrimidinyl}amino)phenyl]carbonyl}amino)ethyl]amino}carbonyl)-2-(6-hydroxy-3-oxo-3H-xanthen-9-yl) benzoic acid, prepared as described in WO2011/120025) was used at a final assay concentration of 5 nM. Both the enzyme and ligand were prepared in solutions in 50 mM HEPES pH7.5, 150 mM NaCl, 10 mM MgCl$_2$, 1 mM DTT, and 1 mM CHAPS. Test compounds were prepared in 100% DMSO and 100 nL was dispensed to individual wells of a multiwell plate. Next, 5 ul RIPK2 was added to the test compounds at twice the final assay concentration, and incubated at rt for 10 min. Following the incubation, 5 ul of the fluorescent labeled ligand solution, was added to each reaction, at twice the final assay concentration, and incubated at rt for at least 10 min. Finally, samples were read on an instrument capable of measuring fluorescent polarization. Test compound inhibition was expressed as percent (%) inhibition of internal assay controls.

For concentration/dose response experiments, normalized data were fit and pIC$_{50}$s determined using conventional techniques. The pIC$_{50}$s are averaged to determine a mean value, for a minimum of 2 experiments.

| Example No. | pIC$_{50}$ |
| --- | --- |
| 1 | 8.4 |
| 2(R) | 8.5 |
| 2(S) | 8.5 |
| 4 | 8.2 |
| 5 | 8.3 |
| 6 | 8.4 |
| 7 | 8.3 |
| 8 | 8.3 |
| 10 | 7.8 |

FLAG His Tagged RIPK2 Preparation:

Full-length human RIPK2 (receptor-interacting serine-threonine kinase 2) cDNA was purchased from Invitrogen (Carlsbad, Calif., USA, Clone ID:IOH6368, RIPK2-pENTR 221). Gateway® LR cloning was used to site-specifically recombine RIPK2 downstream to an N-terminal FLAG-6His contained within the destination vector pDEST8-FLAG-His6 according to the protocol described by Invitrogen. Transfection into *Spodoptera frugiperda* (Sf9) insect cells was performed using Cellfectin® (Invitrogen), according to the manufacturer's protocol.

Sf9 cells were grown in Excell 420 (SAFC Biosciences, Lenexa, Kans., US; Andover, Hampshire UK) growth media at 27° C., 80 rpm in shake flask until of a sufficient volume to inoculate a bioreactor. The cells were grown in a 50 liter working volume bioreactor (Applikon, Foster City, Calif., US; Schiedam, Netherlands) at 27° C., 30% dissolved oxygen and an agitation rate of 60-140 rpm until the required volume was achieved with a cell concentration of approximately 3.7× e6 cells/mL. The insect cells were infected with Baculovirus at a multiplicity of infection (MOI) of 12.7. The cultivation was continued for a 43 hour expression phase. The infected cells were removed from the growth media by centrifugation at 2500 g using a Viafuge (Carr) continuous centrifuge at a flow rate of 80 liters/hour. The cell pellet was immediately frozen and subsequently supplied for purification.

Purification Procedure I: $9.83 \times 10^{10}$ Insect cells were re-suspended in 1.4 L lysis buffer (50 mM Tris (pH 8.0), 150 mM NaCl, 0.5 mM NaF, 0.1% Triton X-100, 1 mL/liter Protease Inhibitor Cocktail Set III (available from EMD Group; Cal-Biochem/Merck Biosciences, Gibbstown, N.J., US; Damstadt, Germany) and processed by dounce homogenization on ice. The suspension was then clarified by centrifugation at 47,900 g for 2 h, at 4° C. The lysate was decanted from the insoluble pellet and loaded at a linear flow rate of 16 cm/h onto a 55 mL FLAG-M2 affinity column (2.6×10.4 cm) that had been pre-equilibrated with 10 column volumes buffer A (50 mM Tris (pH 8.0), 150 mM NaCl, 0.5 mM NaF, 1 mL/liter Protease Inhibitor Cocktail Set III). The column was then washed with 15 column volumes buffer A, and eluted with 6 column volumes buffer B (buffer A+150 µg/mL 3× FLAG peptide) at a linear flow rate of 57 cm/h. Fractions identified by SDS-PAGE as containing protein of interest were dialyzed to remove the 3× FLAG peptide from the preparation against 5 L of Buffer A (not containing the Protease Inhibitor Cocktail) overnight, using 10 kDa MWCO SnakeSkin Pleated Dialysis Tubing. The purification process yielded 11.3 mg of total protein, with the RIPK2 present at 40% purity by gel densitometry scanning, and identity confirmed by peptide mass fingerprinting. The main contaminating proteins in the preparation were identified as lower molecular weight degraded species of RIPK2.

Purification Procedure II: 100 g cells (10 liter scale fermentation) were frozen, thawed, and re-suspended in 1 L lysis buffer (50 mM Tris HCL pH7.5, 250 mM NaCl, 0.1 mM TCEP, 3 ml Protease inhibitor cocktail) and lysed by high pressure homogenization at 10,000 psi once (Avestin). The suspension was then clarified by centrifugation at 35,000 g for 45 minutes at 4° C. The supernatant was collected by centrifugation and incubated with 5 ml anti-FLAG-M2 resin which was pre-equilibrated with buffer A (50 mM Tris HCL pH7.5, 250 mM NaCl, 0.1 mM TCEP). After protein binding at 4 degree C. for 1 hour, the resin was packed into two 25 ml disposable columns. Each column was washed with 25 ml buffer A and eluted with 10 ml (buffer A+200 ug/ml Flag peptide). The elution pool was concentrated to 1 ml and applied to a superdex 200 (16/60) sizing column. Fractions containing full length RIPK2 were collected according to SDS-PAGE analysis results. The purification process yielded 1.36 mg/L 80% pure RIPK2 protein and identity was confirmed by peptide mass fingerprinting.

Biological In Vivo Assay

The efficacy of RIP2 inhibitors may also be evaluated in vivo in rodents. Intraperitoneal (i.p.) or intravenous (i.v.) administration of L18-MDP in mice has been shown to induce an inflammatory response through activation of the NOD2 signaling pathway (Rosenweig, H. L., et al. 2008. Journal of Leukocyte Biology 84:529-536). The level of the inflammatory response in the L18-MDP treated mice/rats is monitored using conventional techniques by measuring increases in cytokine levels (IL8, TNFα, IL6 and IL-1β) in serum and/or peritoneal lavage fluid and by measuring neutrophil influx into the peritoneal space (when L18-MDP is dosed i.p.) Inhibition of the L18-MDP induced inflammatory response in treated rodents may be shown by orally pre-dosing with selected compounds of this invention, then measuring and comparing cytokine levels (IL8, TNFα, IL6 and IL-1β) in serum and/or peritoneal lavage fluid and neutrophil influx into the peritoneal space (when L18-MDP is dosed i.p.) using conventional techniques.

Figure 3:
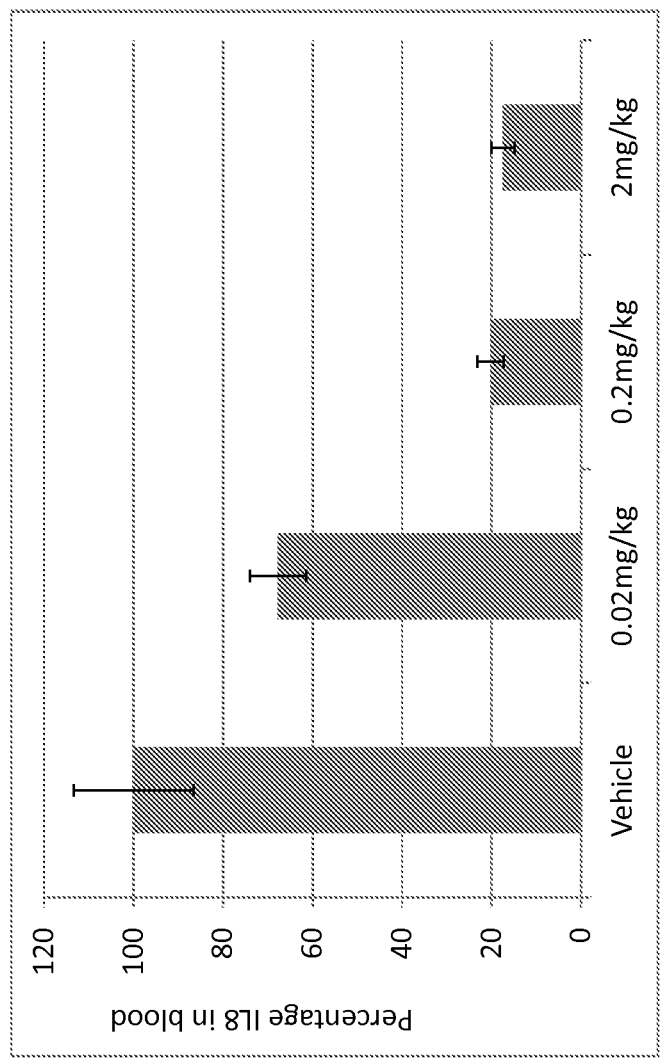
FIG. 3 shows the IL-8 cytokine response in rat whole blood samples obtained after pre-dosing rats with the compound of Example 3, followed by dosing with L18-MDP.

For example, rats were orally pre-dosed with the compound of Example 3, at doses of 0.02, 0.2 and 2 mg/kg (n=8 rats/group), followed by dosing with L18-MDP (50 µg/rat) 0.25 hours after pre-dosing with the compound. IL8 cytokine levels in whole blood samples taken from the rats in this study were measured using an antibody based detection (Meso-Scale Discovery platform). The IL8 cytokine percentage levels were calculated as the relative levels observed to the vehicle-treated rats, and are depicted in FIG. 3 as the mean±standard error of the mean (n=8 rats/group).

Figure 4:
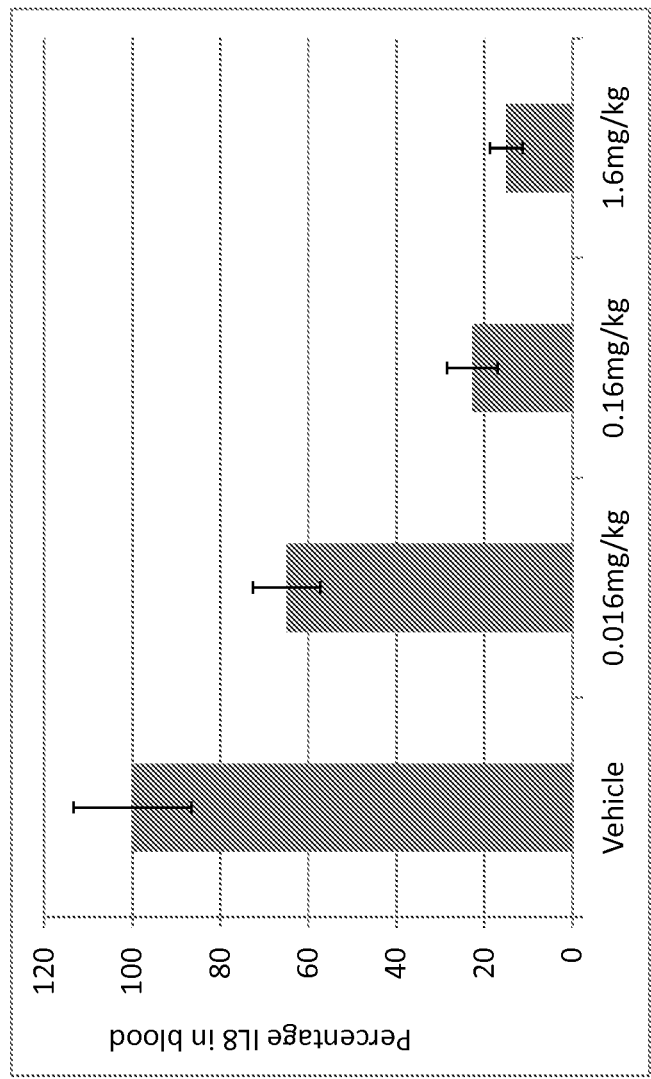
FIG. 4 shows the IL-8 cytokine response in rat whole blood samples obtained after pre-dosing rats with the compound of Example 9, followed by dosing with L18-MDP.

In another example, rats were orally pre-dosed with the compound of Example 9, at doses of 0.016, 0.16 and 1.6 mg/kg (n=8 rats/group), followed by dosing with L18-MDP (50 µg/rat) 0.25 hours after pre-dosing with the compound. The IL8 cytokine levels and percentage levels were calculated as described above and are depicted in FIG. 4 as the mean±standard error of the mean (n=8 rats/group).

References: WO 98/13350, WO2011/120025, WO2011/120026, WO2011/123609, WO2011/140442, WO2012/021580, WO2012/122011, WO2013/025958, *Bioorg. Med. Chem. Lett.* (2007), 17(21), 5886-5893

What is claimed is:

1. A compound which is:

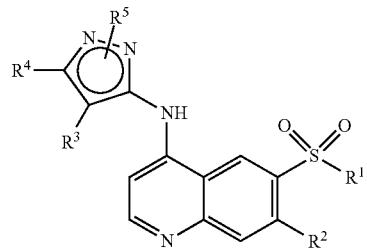

wherein:
R$^1$ is —C(CH$_3$)$_3$;
R$^2$ is —OCH$_2$CH$_2$OCH$_3$;
R$^3$ is methyl;
R$^4$ is methyl; and
R$^5$ is H;
or a pharmaceutically acceptable salt thereof, or hydrate thereof.

2. A compound which is

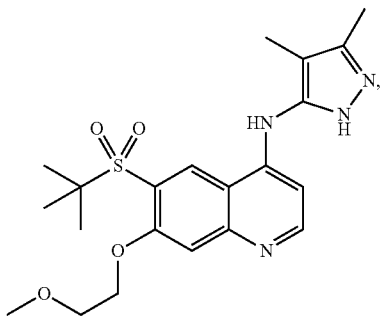 [SMILES: COCCOc1cc2nccc(Nc3[nH]nc(C)c3C)c2cc1S(=O)(=O)C(C)(C)C]

or a pharmaceutically acceptable salt thereof.

3. The compound, or pharmaceutically acceptable salt thereof, or hydrate thereof, according to claim 1, which is the free base of said compound.

4. The compound, or pharmaceutically acceptable salt thereof, or hydrate thereof, according to claim 1, which is the pharmaceutically acceptable salt of said compound.

5. The compound, or pharmaceutically acceptable salt thereof, or hydrate thereof, according to claim 1, which is the hydrate of the pharmaceutically acceptable salt of said compound.

6. The compound, or pharmaceutically acceptable salt thereof, or hydrate thereof, according to claim 4, wherein the pharmaceutically acceptable salt is a hydrochloride salt.

7. The compound, or pharmaceutically acceptable salt thereof, or hydrate thereof, according to claim 5, which is the hydrate of a hydrochloride salt of said compound.

8. The compound, or pharmaceutically acceptable salt thereof, or hydrate thereof, according to claim 5, which is a monohydrate of a hydrochloride salt of said compound.

9. A compound which is:

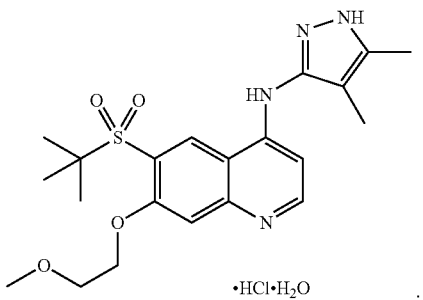

·HCl·H$_2$O

10. The compound according to claim 9, having the PXRD according to FIG. 2.

11. A pharmaceutical composition comprising the compound, or pharmaceutically acceptable salt thereof, or hydrate thereof, according to claim 1, and one or more pharmaceutically acceptable excipients.

12. A method of treating a disease or disorder mediated by inhibition of RIP2 kinase comprising administering a therapeutically effective amount of the compound, or pharmaceutically acceptable salt thereof, or hydrate thereof, according to claim 1, to a human in need thereof, wherein the disease mediated by inhibition of RIP2 kinase is selected from uveitis, interleukin-1 converting enzyme associated fever syndrome, dermatitis, acute lung injury, type 2 diabetes mellitus, arthritis, rheumatoid arthritis, ulcerative colitis, Crohn's disease, early-onset inflammatory bowel disease, extraintestinal inflammatory bowel disease, prevention of ischemia reperfusion injury in solid organ transplant, non-alcohol steatohepatitis, alcohol steatohepatitis, autoimmune hepatitis, asthma, graft versus host disease, systemic lupus erythematosus, multiple sclerosis, sarcoidosis, Blau syndrome/early-onset sarcoidosis, Wegner's granulomatosis, and interstitial pulmonary disease.

13. A method of treating a disease or disorder mediated by inhibition of RIP2 kinase comprising administering a therapeutically effective amount of the compound, or pharmaceutically acceptable salt thereof, or hydrate thereof, according to claim 1, to a human in need thereof, wherein the disease or disorder is selected from the group consisting of uveitis, interleukin-1 converting enzyme associated fever syndrome, Blau Syndrome, early-onset sarcoidosis, ulcerative colitis, Crohn's disease, Wegener's granulamatosis and sarcoidosis.

14. The method according to claim 11, wherein the disease or disorder is Crohn's disease.

15. The method according to claim 11, wherein the disease or disorder is ulcerative colitis.

16. The method according to claim 11, wherein the disease or disorder is Blau syndrome.

* * * * *